(12) United States Patent
Higashio et al.

(10) Patent No.: US 6,333,309 B1
(45) Date of Patent: *Dec. 25, 2001

(54) HUMAN-DERIVED GLYCOPROTEIN, BIOLOGICALLY ACTIVE FACTOR WHICH INCLUDES GLYCOPROTEIN, AND PHARMACEUTICAL PRODUCT WHICH COMPRISES BIOLOGICALLY ACTIVE FACTOR AS ACTIVE COMPONENT

(75) Inventors: Kanji Higashio; Shinjiro Mitsuda; Nobuyuki Shima, all of Saitama; Yasuharu Itagaki; Masaya Nagao, both of Tochigi, all of (JP)

(73) Assignee: Snow Brand Milk Products Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/617,621

(22) Filed: Mar. 19, 1996

Related U.S. Application Data

(62) Division of application No. 08/304,419, filed on Sep. 12, 1994, now Pat. No. 5,587,359.

(30) Foreign Application Priority Data

Mar. 10, 1989 (JP) .................................... 1-58631

Jan. 16, 1990 (JP) .................................... 2-6692

(51) Int. Cl.$^7$ ............................ A61K 7/46; C07K 14/00
(52) U.S. Cl. ........................... 514/12; 530/350; 530/399
(58) Field of Search ........................... 514/12; 530/399, 530/350

(56) References Cited

U.S. PATENT DOCUMENTS

| 4,992,419 | * | 2/1991 | Woog et al. | 514/8 |
| 5,004,805 | * | 4/1991 | Gohda et al. | 530/399 |
| 5,037,644 | * | 8/1991 | Shaked et al. | 424/85.2 |

OTHER PUBLICATIONS

Capaldi et al. 1977. Biochem. Biophys. Res. Commun. 74(2): 425–433.*
Gohda et al 1988 J Clin Invest. 81:414–419.*
Miyazawa et al 1989 Biochem. Biophys. Res. Commun. 163:967–973.*

* cited by examiner

*Primary Examiner*—Karen Cochrane Carlson
(74) *Attorney, Agent, or Firm*—Burgess, Ryan & Wayne; Milton J. Wayne; William R. Moran

(57) ABSTRACT

The new glycoprotein, which possesses an anti-tumor activity, a leukemia cell differentiation inducing activity, a cellular immunology enhancing activity, a vascular endothelial cell growth stimulating activity and a hepatocyte growth stimulating activity, can be obtained.

9 Claims, 18 Drawing Sheets

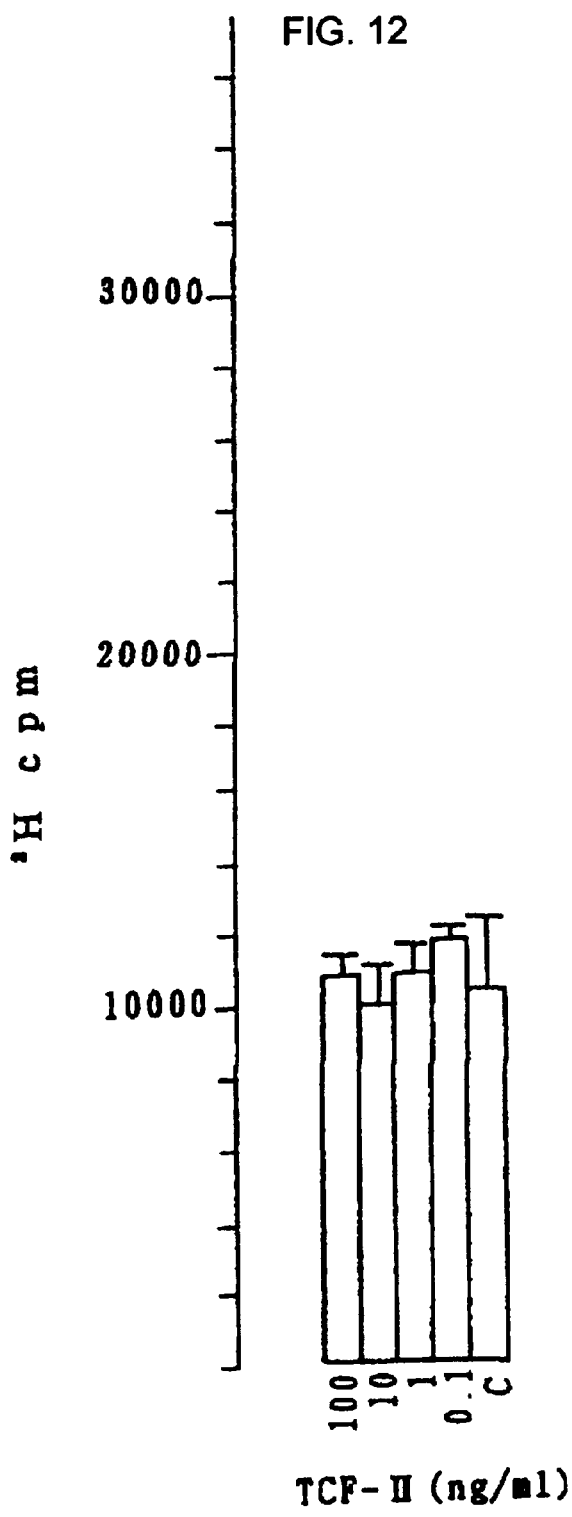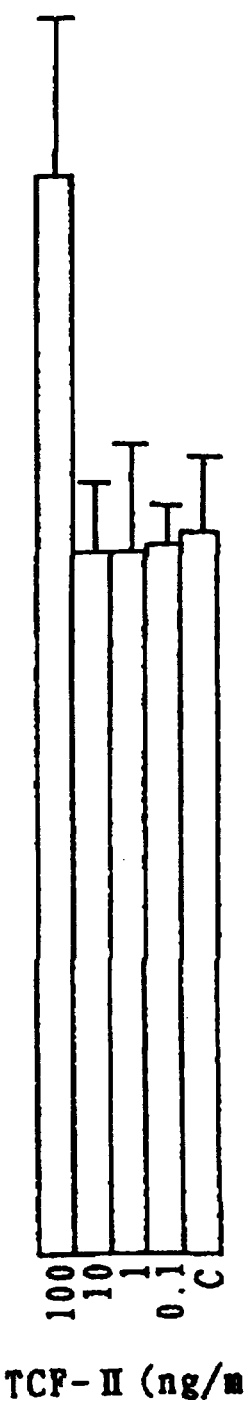
FIG. 12
FIG. 13

Fig. 15 (a)

```
                                                          -70              -60
                                                       TAGGCACTGACTCCGAA

-50          -40         -30         -20         -10            0
      CAGGATTCTTTCACCCAGGCATCTCCTCCAGAGGGATCCGCCAGCCCGTCCAGCAGCACC 10          20          30          40          50           60
      ATGTGGGTGACCAAACTCCTGCCAGCCCTGCTGCTGCAGCATGTCCTCCTGCATCTCCTC
       M  W  V  T  K  L  L  P  A  L  L  L  Q  H  V  L  L  H  L  L 70          80          90         100         110          120
      CTGCTCCCCATCGCCATCCCCTATGCAGAGGGACAAAGGAAAAGAAGAAATACAATTCAT
       L  L  P  I  A  I  P  Y  A  E  G  Q  R  K  R  R  N  T  I  H 130         140         150         160         170          180
      GAATTCAAAAAATCAGCAAAGACTACCCTAATCAAAATAGATCCAGCACTGAAGATAAAA
       E  F  K  K  S  A  K  T  T  L  I  K  I  D  P  A  L  K  I  K 190         200         210         220         230          240
      ACCAAAAAAGTGAATACTGCAGACCAATGTGCTAATAGATGTACTAGGAATAAAGGACTT
       T  K  K  V  N  T  A  D  Q  C  A  N  R  C  T  R  N  K  G  L 250         260         270         280         290          300
      CCATTCACTTGCAAGGCTTTTGTTTTTGATAAAGCAAGAAAACAATGCCTCTGGTTCCCC
       P  F  T  C  K  A  F  V  F  D  K  A  R  K  Q  C  L  W  F  P 310         320         330         340         350          360
      TTCAATAGCATGTCAAGTGGAGTGAAAAAAGAATTTGGCCATGAATTTGACCTCTATGAA
       F  N  S  M  S  S  G  V  K  K  E  F  G  H  E  F  D  L  Y  E 370         380         390         400         410          420
      AACAAAGACTACATTAGAAACTGCATCATTGGTAAAGGACGCAGCTACAAGGGAACAGTA
       N  K  D  Y  I  R  N  C  I  I  G  K  G  R  S  Y  K  G  T  V 430         440         450         460         470          480
      TCTATCACTAAGAGTGGCATCAAATGTCAGCCCTGGAGTTCCATGATACCACACGAACAC
       S  I  T  K  S  G  I  K  C  Q  P  W  S  S  M  I  P  H  E  H 490         500         510         520         530          540
      AGCTATCGGGGTAAAGACCTACAGGAAAACTACTGTCGAAATCCTCGAGGGGAAGAAGGG
       S  Y  R  G  K  D  L  Q  E  N  Y  C  R  N  P  R  G  E  E  G 550         560         570         580         590          600
      GGACCCTGGTGTTTCACAAGCAATCCAGAGGTACGCTACGAAGTCTGTGACATTCCTCAG
       G  P  W  C  F  T  S  N  P  E  V  R  Y  E  V  C  D  I  P  Q 610         620         630         640         650          660
      TGTTCAGAAGTTGAATGCATG::CCTGCAATGGGGAGAGTTATCGAGGTCTCATGGATCAT
       C  S  E  V  E  C  M  T  C  N  G  E  S  Y  R  G  L  M  D  H 670         680         690         700         710          720
      ACAGAATCAGGCAAGATTTGTCAGCGCTGGGATCATCAGACACCACACCGGCACAAATTC
       T  E  S  G  K  I  C  Q  R  W  D  H  Q  T  P  H  R  H  K  F 730         740         750         760         770          780
      TTGCCTGAAAGATATCCCGACAAGGGCTTTGATGATAATTATTGCCGCAATCCCGATGGC
       L  P  E  R  Y  P  D  K  G  F  D  D  N  Y  C  R  N  P  D  G 790         800         810         820         830          840
      CAGCCGAGGCCATGGTGCTATACTCTTGACCCTCACACCCGCTGGGAGTACTGTGCAATT
       Q  P  R  P  W  C  Y  T  L  D  P  H  T  R  W  E  Y  C  A  I 850         860         870         880         890          900
      AAAACATGCGCTGACAATACTATGAATGACACTGATGTTCCTTTGGAAACAACTGAATGC
       K  T  C  A  D  N  T  M  N  D  T  D  V  P  L  E  T  T  E  C 910         920         930         940         950          960
      ATCCAAGGTCAAGGAGAAGGCTACAGGGGCACTGTCAATACCATTTGGAATGGAATTCCA
       I  Q  G  Q  G  E  G  Y  R  G  T  V  N  T  I  W  N  G  I  P 970         980         990        1000        1010         1020
      TGTCAGCGTTGGGATTCTCAGTATCCTCACGAGCATGACATGACTCCTGAAAATTTCAAG
       C  Q  R  W  D  S  Q  Y  P  H  E  H  D  M  T  P  E  N  F  K 1030        1040        1050        1060        1070         1080
      TGCAAGGACCTACGAGAAAATTACTGCCGAAATCCAGATGGGTCTGAATCACCCTGGTGT
       C  K  D  L  R  E  N  Y  C  R  N  P  D  G  S  E  S  P  W  C 1090        1100        1110        1120        1130         1140
      TTTACCACTGATCCAAACATCCGAGTTGGCTACTGCTCCCAAATTCCAAACTGTGATATG
       F  T  T  D  P  N  I  R  V  G  Y  C  S  Q  I  P  N  C  D  M
```

Fig. 15 (b)

```
          1150      1160      1170      1180      1190      1200
     TCACATGGACAAGATTGTTATCGTGGGAATGGCAAAAATTATATGGGCAACTTATCCCAA
      S  H  G  Q  D  C  Y  R  G  N  G  K  N  Y  M  G  N  L  S  Q
                                                                    internal amino acid sequence
          1210      1220      1230      1240      1250      1260           in α-chain
     ACAAGATCTGGACTAACATGTTCAATGTGGGACAAGAACATGGAAGACTTACATCGTCAT
      T  R  S  G  L  T  C  S  H  W  D  K  N  M  E  D  L  H  R  H 1270      1280      1290      1300      1310      1320
     ATCTTCTGGGAACCAGATGCAAGTAAGCTGAATGAGAATTACTGCCGAAATCCAGATGAT
      I  F  W  E  P  D  A  S  K  L  N· E  N  Y  C  R  N  P  D  D 1330      1340      1350      1360      1370      1380
     GATGCTCATGGACCCTGGTGCTACACGGGAAATCCACTCATTCCTTGGGATTATTGCCCT
      D  A  H  G  P  W  C  Y  T  G  N  P  L  I  P  W  D  Y  C  P 1390      1400      1410      1420      1430      1440
     ATTTCTCGTTGTGAAGGTGATACCACACCTACAATAGTCAATTTAGACCATCCCGTAATA
      I  S  R  C  E  G  D  T  T  P  T  I  V  N  L  D  H  P  Y  I 1450      1460      1470      1480      1490      1500
     TCTTGTGCCAAAACGAAACAATTGCGAGTTGTAAATGGGATTCCAACACGAACAAACATA
      S  C  A  K  T  K  Q  L  R  V  Y  N  G  I  P  T  R  T  N  I
                                    ↑
                              N-terminal in β chain       N-terminal amino acid sequence
          1510      1520      1530      1540      1550      1560           in β-chain
     GGATGGATGGTTAGTTTGAGATACAGAAATAAACATATCTGCGGAGGATCATTGATAAAG
      G  W  M  V  S  L  R  Y  R  N  K  H  I  C  G  G  S  L  I  K 1570      1580      1590      1600      1610      1620
     GACAGTTGGGTTCTTACTGCACGACAGTGTTTCCCTTCTCGAGACTTGAAAGATTATGAA
      E  S  W  V  L  T  A  R  Q  C  F  P  S  R  D  L  K  D  Y  E 1630      1640      1650      1660      1670      1680
     GCTTGGCTTGGAATTCATGATGTCCACGGAAGAGGAGATGAGAAATGCAAACAGGTTCTC
      A  W  L  G  I  H  D  V  H  G  R  G  D  E  K  C  K  Q  V  L 1690      1700      1710      1720      1730      1740
     AATGTTTCCCAGCTGGTATATGGCCCTGAAGGATCAGATCTGGTTTTAATGAAGCTTGCC
      N  V  S  Q  L  Y  Y  G  P  E  G  S  D  L  V  L  M  K  L  A 1750      1760      1770      1780      1790      1800
     AGGCCTGCTGTCCTGGATGATTTTGTTAGTACGATTGATTTACCTAATTATGGATGCACA
      R  P  A  V  L  D  D  F  V  S  T  I  D  L  P  N  Y  G  C  T 1810      1820      1830      1840      1850      1860
     ATTCCTGAAAAGACCAGTTGCAGTGTTTATGGCTGGGGCTACACTGGATTGATCAACTAT
      I  P  E  K  T  S  C  S  V  Y  G  W  G  Y  T  G  L  I  N  Y
                                                                    internal amino acid sequence
          1870      1880      1890      1900      1910      1920           in β-chain
     GATGGCCTATTACGAGTGGCACATCTCTATATAATGGGAAATGAGAAATGCAGCCAGCAT
      D  G  L  L  R  V  A  H  L  Y  I  M  G  N  E  K  C  S  Q  H 1930      1940      1950      1960      1970      1980
     CATCGAGGGAAGGTGACTCTGAATGAGTCTGAAATATGTGCTGGGGCTGAAAAGATTGGA
      H  R  G  K  V  T  L  N  E  S  E  I  C  A  G  A  E  K  I  G 1990      2000      2010      2020      2030      2040
     TCAGGACCATGTGAGGGGGATTATGGTGGCCCACTTGTTTGTGAGCAACATAAAATGAGA
      S  G  P  C  E  G  D  Y  G  G  P  L  V  C  E  Q  H  K  M  R 2050      2060      2070      2080      2090      2100
     ATGGTTCTTGGTGTCATTGTTCCTGGTCGTGGATGTGCCATTCCAAATCGTCCTGGTATT
      M  V  L  G  V  I  V  P  G  R  G  C  A  I  P  N  R  P  G  I 2110      2120      2130      2140      2150      2160
     TTTGTCCGAGTAGCATATTATGCAAAATGGATACACAAAATTATTTTAACATATAAGGTA
      F  V  R  V  A  Y  Y  A  K  W  I  H  K  I  I  L  T  Y  K  V 2170      2180      2190      2200      2210
     CCACAGTCATAGCTGAAGTAAGTGTGTCTGAAGCACCCACCAATACAACTGT
      P  Q  S  *
```

```
  1 MWVTKLLPALLLQHVLLHLLLLPIAIPYAEGQRKRRNTIHEFKKSAKTTLIKIDPALKIK
    ************************************************************
    MWVTKLLPALLLQHVLLHLLLLPIAIPYAEGQRKRRNTIHEFKKSAKTTLIKIDPALKIK
  1

61 TKKVNTADQCANRCTRNKGLPFTCKAFVFDKARKQCLWFPFNSMSSGVKKEFGHEFDLYE
    ************************************************************
    TKKVNTADQCANRCTRNKGLPFTCKAFVFDKARKQCLWFPFNSMSSGVKKEFGHEFDLYE
 61

121 NKDYIRNCIIGKGRSYKGTVSITKSGIKCQPWSSMIPHEH-----SYRGKDLQENYCRNP
    ****************************************    ***************
    NKDYIRNCIIGKGRSYKGTVSITKSGIKCQPWSSMIPHEHSFLPSSYRGKDLQENYCRNP
121

176 RGEEGGPWCFTSNPEVRYEVCDIPQCSEVECMTCNGESYRGLMDHTESGKICQRWDHQTP
    ************************************************************
    RGEEGGPWCFTSNPEVRYEVCDIPQCSEVECMTCNGESYRGLMDHTESGKICQRWDHQTP
181

236 HRHKFLPERYPDKGFDDNYCRNPDGQPRPWCYTLDPHTRWEYCAIKTCADNTMNDTDVPL
    ************************************************************
    HRHKFLPERYPDKGFDDNYCRNPDGQPRPWCYTLDPHTRWEYCAIKTCADNTMNDTDVPL
241
```

FIG. 16A

```
296 ETTECIQGQGEGYRGTVNTIWNGIPCQRWDSQYPHEHDMTPENFKCKDLRENYCRNPDGS
    ************************************************************
301 ETTECIQGQGEGYRGTVNTIWNGIPCQRWDSQYPHEHDMTPENFKCKDLRENYCRNPDGS

356 ESPWCFTTDPNIRVGYCSQIPNCDMSHGQDCYRGNGKNYMGNLSQTRSGLTCSMWDKNME
    ************************************************************
361 ESPWCFTTDPNIRVGYCSQIPNCDMSHGQDCYRGNGKNYMGNLSQTRSGLTCSMWDKNME

416 DLHRHIFWEPDASKLNENYCRNPDDDAHGPWCYTGNPLIPWDYCPISRCEGDTTPTIVNL
    ************************************************************
421 DLHRHIFWEPDASKLNENYCRNPDDDAHGPWCYTGNPLIPWDYCPISRCEGDTTPTIVNL

476 DHPVISCAKTKQLRVVNGIPTRTNIGWMVSLRYRNKHICGGSLIKESWVLTARQCFPSRD
    ************************************************************
481 DHPVISCAKTKQLRVVNGIPTRTNIGWMVSLRYRNKHICGGSLIKESWVLTARQCFPSRD

536 LKDYEAWLGIHDVHGRGDEKCKQVLNVSQLVYGPEGSDLVLMKLARPAVLDDFVSTIDLP
    ************************************************************
541 LKDYEAWLGIHDVHGRGDEKCKQVLNVSQLVYGPEGSDLVLMKLARPAVLDDFVSTIDLP

```
601 NYGCTIPEKTSCSVYGWGYTGLINYDGLLRVAHLYIMGNEKCSQHHRGKVTLNESEICAG
    ************************************************************
656 NYGCTIPEKTSCSVYGWGYTGLINYDGLLRVAHLYIMGNEKCSQHHRGKVTLNESEICAG

661 AEKIGSGPCEGDYGGPLVCEQHKMRMVLGVIVPGRGCAIPNRPGIFVRVAYYAKWIHKII
    ************************************************************
    AEKIGSGPCEGDYGGPLVCEQHKMRMVLGVIVPGRGCAIPNRPGIFVRVAYYAKWIHKII 716     723
    LTYKVPQS
    ********
    LTYKVPQS
721     728
```

FIG. 16C

HUMAN-DERIVED GLYCOPROTEIN, BIOLOGICALLY ACTIVE FACTOR WHICH INCLUDES GLYCOPROTEIN, AND PHARMACEUTICAL PRODUCT WHICH COMPRISES BIOLOGICALLY ACTIVE FACTOR AS ACTIVE COMPONENT

This is a division of application Ser. No. 08/304,419, filed Sep. 12, 1994 now U.S. Pat. No. 5,587,359.

FIELD OF THE INVENTION

The present invention relates to a glycoprotein obtained from the culture broth of the human-derived fibroblasts, biologically active factor which includes glycoprotein, and pharmaceutical composition which comprises biologically active factor as active component.

The glycoprotein in the present invention, which shows cytotoxic activity to various tumor cell lines but not to normal cells, is a new tumor cytotoxic factor, leukemic cell differentiation inducing factor, cellular immunology enhancing factor, vascular endothelial cell growth factor and hepatocyte growth factor. This material is useful as an anti-tumor drug, an anti leukemia drug, a cellular immunology enhancing drug, a wound healing drug and a liver regenerating drug, etc. or a biochemical or pharmacological reagent.

DESCRIPTION OF THE RELATED ART

β-Interferon is a representative factor as the biologically active factor, for example, the tumor cytotoxic factor which is produced by human-derived fibroblasts. This is a glycoprotein which is secreted by the fibroblasts, when after the culture, the cells are harvested and stimulated by poly I-polyC or sendai viruses. It has been clarified that the protein has various physiological activities in addition to its anti virus or anti-tumor action. A fibroblast-derived tumor cytotoxic glycoprotein called as CBF is represented in Japanese Laid-Open No. 58-146293. A tumor growth inhibitory factor (INF) with a molecular weight of 35,000 to 45,000 which is purified from the culture broth of human tissue-derived fibroblasts is disclosed in Japanese Laid Open No. 671-33120. Also, a tumor necrosis factor-like material which is purified from the culture broth of fibroblasts, a fibroblast-derived necrosis factor, FNF, and a biologically active material with the cytotoxic activity, which is produced by animal fibroblast cells and has a molecular weight of 40,000 to 50,000 and an isoelectric point of 5.0±0.5, are disclosed in Japanese Laid Open No. 61-56131, Japanese Laid Open No. 61-1872, and Japanese Laid Open No. 62-103021, respectively. Furthermore, all amino acid sequence and cDNA sequence coding for the amino acid sequence of a tumor cytotoxic factor, which is obtained from the culture broth of human-derived fibroblasts, with a molecular weight of 36,000±1,000 and an isoelectric point more than 10.5, are disclosed in Japanese Laid Open No. 64-10998.

SUMMARY OF THE INVENTION

The present inventors have investigated a biologically active material which is contained in the culture broth of human-derived fibroblasts and have found a glycoprotein with various biological activities and, which is different from the materials reported previously with respect to the molecular weight and the isoelectric point etc.

Therefore, the main aim of the present invention is to offer 1 new glycoprotein, biologically active factor which includes said glycoprotein, and pharmaceutical product which comprises said biologically active factor.

A new human fibroblast-derived glycoprotein in the present invention (it is referred to as TCF-II hereafter) is characterized by the following physichochemical properties.

a. Molecular weight; On SDS gel electrophoresis, 78,000±2,000 or 74,000±2,000 under the nonreduced conditions and a common band A with 52,000±2,000 and band B with 30,000±2,000 or band C with 26,000±2,000 under the reduced conditions.

b. Isoelectric point; 7.4 to 8.6.

c. Heat stability; Stable in the heating at 60° C. for 10 min.

d. pH stability; Stable in the range of pH6 to 9.

e. Carbohydrate chain; Adsorbed to a Concanavalin A (Con A)-Sepharose column.

f. Biological activity; Inhibit the growth of KB cells, HeLa cells, and L-929 cells but not IMR-90 cells.

g. Reactivity to antibodies; The cytotoxic activity is not neutralized by anti-TNF antibody, anti-lymphotoxin antibody, and anti-interferon-β antibody.

Furthermore, the suitable lot of TCF-II in the present invention has the following properties in addition to the above physicochemical characteristics (a~g):

h. N-terminal amino acid sequence; The above mentioned band B and band C are subchains of band A, respectively. N-terminus of band A is blocked. Band B and band C has a common N-terminal amino acid sequence as follows;

Val-Val-Asn-Gly-Ile-Pro-Thr- or

Val-Val-Asn-Gly-Ile-Pro-Thr-X-Thr-Asn-Ile-Gly-X-Met-Val-Ser-Leu-

X means an unidentified amino acid.

i. Amino acid composition; When it is hydrolyzed with HCl it exhibits the following amino acid composition.

| A.A | nmol | mol % |
|---|---|---|
| Asp | 10.375 | 12.97 |
| Glu | 7.750 | 9.69 |
| Ser | 5.000 | 6.25 |
| Gly | 7.250 | 9.06 |
| His | 3.000 | 3.75 |
| Arg | 5.375 | 6.72 |
| Thr | 5.125 | 6.41 |
| Ala | 2.625 | 3.28 |
| Pro | 5.625 | 7.03 |
| Tyr | 3.875 | 4.84 |
| Val | 4.125 | 5.16 |
| Met | 1.875 | 2.34 |
| Cys | ND | — |
| Ile | 5.000 | 6.25 |
| Leu | 4.875 | 6.09 |
| Phe | 2.250 | 2.81 |
| Trp | ND | — |
| Lys | 5.875 | 7.34 |
| total | 80.000 | 100(99.99) |

Furthermore, all the primary sequence of TCF-II in the present invention was deduced from its complementary DNA (cDNA). TCF-II cDNA was cloned by screening cDNA library which was prepared by using mRNA purified from total RNA which was extracted from human embryonic fibroblast cells (IMR-90), according to the following method.

(1) Extraction of Poly(A)$^+$ RNA from IMR-90 Cells

Total RNA was prepared by guanidine thiocyanatecesium chloride method (Biochemistry 18 5294-5299(1979)) from $2 \times 10^8$ IMR-90 cells which were cultured in the Dulbecco's modified eagle (DME) medium containing 5% of new born calf serum (NBCS). The IMR-90 cells were suspended in 28 ml of 6M guanidine thiocyanate containing BmM sodium citrate, 0.5% Sarcoseal and 0.1M β-mercaptoethanol, and were homogenized. 5.7M cesium chroride solution, 4 ml containing 0.1M EDTA was put into polyallomer centrifuge tubes. The homogenized solution, 7 ml was loaded on the cesium chloride solution and then centrifuged at 35,000 rpm, 20° C. for 16 hours, using 40T1 rotor of Beckman centrifugator. After centrifugation, the pellets were washed twice with 95% ethanol and dissolved in 200 μl of 10 mM Tris HCl buffer (pH7.5) solution containing 1 mM EDTA by heating at 65° C. for min, designated as total RNA solution. Poly (A)$^+$RNA was purified from the total RNA by the method of oligo (dT)cellulose-column chromatography. The total RNA solution was loaded on the oligo (dT) cellulose-column which was equilibrated with 10 mM Tris HCl buffer(pH7.4) solution containing 1 mM EDTA, 0.5M NaCl and 0.05% SDS. The adsorbed fraction was eluted with 10 mM Tris HCl buffer, pH7.4, containing 1 mM EDTA and 0.05% SDS, and designated as poly(A)$^+$ RNA solution.

(2)Synthesis of cDNA Library

Double strand cDNA was synthesized by using poly (A) $^+$ RNA from (1) as a template and by using cDNA synthesis kit (Pharmacia Co. Ltd), and was attached EcoRI adaptor was attached. The method of synthesis was performed according to the protocol of Pharmacia Co.Ltd, except addition of reverse transcriptase (40 units/reaction mixture, Life Science Co. Ltd ) derived from non-sphere disease virus of avian bone marrow at the synthesis of single strand DNA.

(3) Preparation of cDNA Library

The cDNA obtained from (2) was inserted in EcoRI arm (Promega Co. Ltd) of phage vector λ gt10. 3.3 μg of cDNA synthesized from poly(A)$^+$ RNA was dissolved in 150 1 of column buffer, 66 mM Tris-HCl buffer (pH7.6) containing 1 mM spermidine, 10 mM magnesium chloride, 15 mM dithiothreitol and bovine serum albumin (0.2 mg/ml). 5.2 μl of the above solution was mixed with 1 μg of λ gt 10 EcoRI arm, and then precipitated with ethanol. Recombinant phage DNA including both λ gt 10 and cDNA was prepared as follows. The above precipitate was reconstituted in 9 μl of the column buffer and was incubated at 16° C. overnight by adding 1 μl of 10 mM adenosine triphosphate and 1 μl of T4 DNA ligase (350 units/μl).

(4)Screening of cDNA Library (i) Preparation of Oligonucleotide Probe

For preparation of the probe, a mixture of complementary oligonucleotide of 17 mer (384 species mix) corresponding to the amino acid sequence from Val$^1$ to Pro$^6$ in N-terminal amino acid sequence of TCF-II β-chain was synthesized and labelled 5' terminus with T4 polynucleotide kinase (TAKARA SIIUZO) and [γ-$^{32}$P]ATP (Amersham, Co, Ltd). This probe is shown as following; complementary strand used as prove:

(384 species mix)

```
            3'-CACCACTTACCGTAGGG-5'

G   G   G   C   A

A   A       A   T

T   T       T
```

(ii) Screening of Recombinant Phage

About 500 thousand plaques of phage were obtained by in vitro packaging of the recombinant phage DNA solution which was obtained by (3), using Gigapack Gold (Stratagene) and then by infecting to *E. Coli* C600hfl. After adsorption of the plaques to Hybond-N filter (Amersham), they were denatured with alkali, neutralized and baked at 80° C. for 2 hours. Hybridization was performed by the method of Bell et al (Nature 310 775–777, 1984). The first screening was carried out by using the mix probe which was obtained from (1). One clone which would contain TCF-II fragment was found in the positive plaques detected by the first screening.

(5) Cloning of Full Length of TCF-II cDNA

Internal amino acid sequences (one letter code), (α) NYMGNLSQTRSGL and (β) TSXSVYGWGYT-GLINYDGLL (X:not identified) were obtained respectively from α-and β-chains of TCF-II by digesting them with lysylendopeptidase and subsequently by mapping their fragments. N-terminal amino acid sequence of β-chain of TCF-II was coincided with that of β-chain of one of the human hepatocyte growth factors (hHGFs). Moreover, the above mentioned internal amino acid sequences (α) and (β) in TCF-II were located in α- and β-chain of both hHGF, respectively. Therefore, it has been thought that TCF-II is expressed from one of the family of hliGF genes. MIYAAWA et al, (BBRC 163, 967–973 (1989)) and NAKAMURA et al. (Nature. 342, 440–443 (1989)) reported the hIGF cDNAs from placenta and liver cDNA libraries, respectively.

Comparison of all the primary sequence deduced from both hHGF cDNAs revealed differences in amino acids at 14 sites in their sequences. From these results, the presence of the family of hliGF genes was suggested. Identical regions between placenta type and liver type hHGF cDNAs were chosen as primer sequences for Polymerase Chain Reaction (PCR). The identical oligonucleotides of both hHGF cDNAs at 5' and 3' non-coding region were chemically synthesized and screening of TCF-II cDNA was carried out by PCR using them as primers. Sal-77primer which have a cleavage site of restriction enzyme SalI and Sph2203 primer which have a cleavage site of restriction enzyme SphI were synthesized by DNA synthesizer (Applied Co. Ltd). These primers are shown as following:

Sal-77 primer: 5'-GGTCGACTAGGCACTGAC-TCCGAACAGGATTC-3' Sal I

Sph2203 primer:5'-GGCATGCACAGTTGTATTGG-TGGGTGCTTCAG-3' Sph I cloning with PCR method was carried out by following procedures, (i)PCR

| | |
|---|---:|
| cDNA synthesized as described in (2) | 1 μl |
| (dissolved in 150 μl of column buffer) | |
| 20 μM Sal-77 primer | 2.5 μl |
| 20 μM Sph2203 primer | 2.5 μl |
| 10 × PCR reaction solution | 10 μl |
| (100 mM Tris HCl buffer (pH 8.3) containing | |
| 500 mM KCl, 15 mM MgCl$_2$ and 0.1% (W/V) gelatin) | |
| 1.25 mM dGTP, dATP, dTTP, dCTP, mixture | 16 μl |
| Ampli Taq (5 units/μl TAKARASHUZO) | 0.5 μl |
| Distilled water | 67.5 μl |

After the above solutions were mixed in microfuge tube with 0.5 ml volume size and covered on the liquid surface with 100 μl of mineral oil (Sigma Co. Ltd). PCR was carried out by the Quick Thermo System (Japan Genetics Co. Ltd). After pretreatment at 94° C for 7 min, a three-step reaction which consists of annealing reaction, at 550C for 3 min; polymerase reaction, at 72° C. for 2 min; and denature reaction, at 94° C. for 2 min was repeated 35 times. Then the reaction mixture was treated for 3 min at 55° C., and subsequently for 1 min at 72° C. and then returned to room temperature (Each time includes the altering time of temperature). When a part of the reaction mixture was analyzed an electrophoresis using agarose gel, a DNA fragment consisting of about 2.3 kirobases (Kb) which was thought as aimed TCF-II cDNA, was obtained. Then, the DNA which was obtained from four tubes containing the above mentioned reaction mixture was precipitated with ethanol and digested with restrict-ion enzymes, SalI and SphI. After an agarose gel electrophoresis, DNA fragment with about 2.3Kb was recovered by using DE81 paper (Watman Co. Ltd).

(ii) Subcloning

The DNA fragment with 2.3 Kb digested with restriction enzymes, SalI and SphI, which was obtained from (1), was inserted using ligation kit (TAKARA SHUZO) into a vector fragment which was obtained by digestion of plasmid vector pUC18 (Japan gene Co. Ltd) with restriction enzymes, SalI and SphI, and transfected into *Esherichia Coli* DH5α (according to protocol of BRL Co. Ltd). More than 20 subclones could be obtained.

(iii) Determination of Base Sequence

The base sequences of obtained subclones were determined by the dideoxy-method (Sequeanase Ver. 2.0 TOYOBO). Incorporation errors of nucleotides on the Ampi Taq (TAKARA SIJUZO) were corrected by the analysis of base sequences of several subclones. The base sequence of TCF-II cDNA obtained by the above mentioned procedure and amino acid sequence deduced from the base sequence are shown in FIG. 15. It consists of 2172 base pairs (bp) from ATG of initiation codon for transcription to TAG of termination codon. If translated into amino acid, TCF-II consists of 723 amino acids. Amino acid sequence from the first methionine ($Met^1$) to the 29 th alanine ($Ala^{29}$) residues is presumed as a signal sequence. As shown in FIG. 15, TCF-R in which two polypeptides consisting of a chain and β chain are bound by disulfide bond is synthesized initialy as a single chain. Since N-terminus of a chain in TCF-II was blocked, it was unidentified. However, N-terminal amino acid sequence of β chain and a few internal amino acid sequences of TCF-II were determined as above mentioned, and were shown in FIG. 15.

The obtained base sequence of the TCF-II cDNA is very similar to hHGF which has been found by MIYAZAWA et al (Biochemical and Biophysical Reseach Communication 163 967-973 (1989)). TCF-II cDNA, however, deletes five amino acid residues (F-L-P-S-S) from $Phe^{162}$ to $Ser^{166}$ in the amino acid sequence of hIIGF. Therefore, the facts revealed that TCF-II cDNA was a new one of the family of hHGF genes. The comparison between the amino acid sequence of TCF-lI, which is deduced from above mentioned base sequence, and the amino acid sequence of bHGF (MIYAZAWA et al) is shown in FIG. 16.

The method to obtain the new glycoprotein, TCF-II which is characterized by the above mentioned physico-chemical properties is described in the following.

Any human-derived fibroblast can be used as a cell for the production of the material in the present invention. Human embryonic lung-derived fibroblast cells, human embryonic kidney-derived fibroblast cells, and human embryonic prepuce-derived fibroblast cells etc. are given as suitable cells. In the performance of the present invention, IMR-90 cells (ATCC CCL 186) and WI-38 cells (ATCC CCL 75) etc. are preferably suitable.

These cells are grown in serum-enriched medium or serum-free medium which are used in the common cultures. Dulbecco's modified Eagle medium (DMEM) containing 5% bovine calf serum is given as the representative medium. Amino acids, transferin, fatty acids and hormones such as insulin etc. can be added if necessary.

The cells are cultured in the medium, and the standing culture using T flask etc., the floating culture using microcarrier, and the continuous culture using hollow fiber or ceramic carrier are able to be adopted. It is preferable that the culture is carried out in atomosphere with 5% $CO_2$ at 20 to 37° C. as the culture conditions and that the medium is exchanged every 2 to 3 days. After the cell density reaches the optimum, the medium is exchanged every 7 to 10 days and the culture broth is collected. The desired glycoprotein is purified from the collected culture broth.

The collected culture broth is concentrated by UF concentration using a membrane with a pore size of M.W. 6,000. The desired glycoprotein in the UF concentrate is adsorbed on cation exchange resins and then eluted from the resins with buffer containing 0.3~0.6M NaCl. CM Sephadex (Pharmacia) C-50 etc. can be given as the ion exchange resins. The fractions which have the potent cytotoxic activity are collected and subsequently applied to affinity chromatography for glycoprotein. ConA-Sepharose is especially suitable to affinity chromatography for the desired glycoprotein. The affinity column is equilibrated with 0.05M Tris-HCl buffer, pH7.0, containing 0.5M NaCl, and then the above obtained fraction is applied to the column. After washing the column with equilibration buffer, the active material is eluted from the column with an elution buffer containing carbohydrate corresponding to carbohydrate chain attached to the affinity column (or gel) for glycoprotein. When the above mentioned ConA-Sepharose is used, the active material is eluted with the buffer containing α-methyl-D-mannopyranoside. The eluted active fraction is dialyzed against water and lyophilized. The lyophilized active material is dissolved with 0.05M Tris-HCl buffer, pII6.0 to 7.0, containing 0.2M NaCl and is further purified on HPLC using a strong cation exchange column. Mono S (Pharmacia) is especially suitable to the strong cation exchange column. Elution of the active material from the Mono S column is carried out with a gradient from 0 to 1.0M NaCl and the active fractions are collected.

The present active material is eluted at salt intensity of 0.6 to 0.9M. The obtained active fraction is further purified on an affinity chromatography using Heparin-Sepharose (Pharmacia). Elution of the active material from the Heparin-Sepharose column is carried out by a gradient from 0.3 to 2.0M NaCl and the desired material is eluted at salt intensity of 1.0 to 1.5 M. Subsequently, assays for cytotoxic activity of the present inventional material, TCF-II to mouse L929-18 cells and for growth stimulating activity of TCF-II for hepatocytes are mentioned below.

Assay for Cytotoxic Activity

Mouse L929 cells (ATCC CCL1) were subcloned and a subclone with the highest sensitivity to TCF-II in the present invention was selected. Thus, the clone, L -929-18 which had a high sensitivity to the tumor cell cytotoxic factor was obtained.

L-929-18 cells were grown to confluence in DMEM containing 10% FCS, and then the cells were harvested by trypsin treatment. The cells were suspended at a cell density of $6 \times 10^5$ cells/ml in DMEM containing 10% FCS and 1 82 g/ml actinomycin D. 50 μl of DMEM which was prepared in the same way as the cell suspension was added to each well in 96-well microplate (Falcon) and 50 μl of the sample solution which contains the present substance, TCF-II, dissolved in the same DMEM was added to the first dilution well. Both were mixed well and 50 μl of the mixture was subsequently added to the second dilution well. A serially diluted substance was prepared by repeating the above procedures. 50 μl of the cell suspension was inoculated into each well containing a serially diluted substance and the culture was carried out at 37° C. for 2 days in a $CO_2$ incubator. After the culture, the medium was removed gently and the cells were washed twice with saline. The viable cells which adhere to each well were fixed and stained by addition of 50 μl of 0.5% crystal violet in the mixture of methanol and water (1:4) to each well. Each well was washed three times with distilled water and dried, and the crystal violet in each well was extracted with Sorenson's buffer (mixture of 6.1 ml of 0.1 M disodium citrate, 3.9 ml of 0.1N HCl, and 10 ml of ethanol). Absorbance of the extracts at 570 nm was determined by a microtiter spectrophotometer.

Unit of TCF-II (u/ml) was defined as the dilution ratio given 50% cell death.

Assay for Hepatocyte Growth Stimulating Activity

Hepatocytes were separated from Wister male rat by the method of Segren (Method in cell biology, vol. 13, p29, Academic Press, New York, 1976). The obtained hepatocytes were planted on 24 well plastic plates (Falcon) at the cell density of $8.8 \times 10^4$ cells/0.5 ml/well and cultured under the presence of 5% $CO_2$ at 37° C. A Williams E culture medium (Flow Raboratory) which was supplemented with 10% fetal bovine serum (flyclone), 100 u/ml penicillin and 100 μg/ml streptomycin was used as the culture medium (abbreviated below as basal culture medium). After incubation at 37° C. for 24 hours, the culture medium was exchanged with the basal culture medium containing the test samples. The hepatocytes were further cultured for 24 hours and then cultured in the basal culture medium containing 4 μCi/ml (86 Ci/m mol) of $^8H$- thymidine (Amersham) for 2 hours followed by determination of DNA synthesis. When the hepatocytes were labeled with $^3H$-thymidine, the incorporated counts (dpm) were determined from the difference of counts(dpm) which were measured between the presence and absence of 10 mM hydroxyurea on each test groups. After the cells were labeled by the above procedure, the cells were washed twice with cold PBS, 2% percllioric acid and 95% ethanol and dried by air, then dissolved in 0.8 ml of 2% SDS containing 2 mM EDTA and 20 mM NallCOs followed by determination with a liquid scintillation counter.

The result is shown in Table 1.

TABLE 1

| Sample | Concentration (ng/ml) | Hepatocyte growth stimulating activity (dpm/well, × 10₈) |
| --- | --- | --- |
| No addition | — | 21.7 ± 9.2 |
| hEGF | 20 | 239.3 ± 7.2 |
| TCF-II | 1 | 93.7 ± 29.7 |
|  | 10 | 378.5 ± 93.5 |
|  | 100 | 467.4 ± 77.3 | hEGF (WAKUNAGA Pharmacy Co Ltd) was used as the positive control for hepatocyte growth stimulating activity. The results in Table 1 demonstrate that hepatocyte growth stimulating activity of TCF-1 is stronger than that of hEGF.

Nextly, the present invention describes pharmaceutical preparations which contains biologically active factor, TCF-II, as an active component.

The above mentioned biologically active factor in the present invention has following pharmacological activities:

① An antitumor Activity:

TCF-II inhibits the growth of KB, HeLa, MCF-7 and BG-1 which is human-derived tumor cells, and have a cytotoxic activity to mouse L-929 cells, and to Sarcoma 180, Meth A Sarcoma and P388 of tumor cells, but not inhibit the growth of IMR-90 cells which are human-normal cells.

② A leukemia cell differentiation inducing activity:

TCF-II induces the differentiation of the human-derived leukemia cell line, HL-60 to granulocyte like cells.

③ A cellular immunology enhancing activity:

TCF-II stimulates the growth of human cytotoxic T cells

④ A vascular endothelial cell growth stimulating activity:

TCF-II stimulates the growth of human umbilical cord blood vessel-derived endothelial cells.

⑤ A hepatocyte growth stimulating activity:

TCF-II stimulates the growth of adult rat hepatocytes.

These activities are exhibited in very small dose range of 1–1000 ng/ml.

The pharmaceutical composition in the present invention can be expected as an anti-tumor drug, an anti-leukemia drug, a cellular immunology enhancing drug, wound healing drug and therapeutic drug for liver disease including liver regenerating drug and so on. The biologically active factor (it is referred to as TCF-II hereafter) which is a glycoprotein with high molecular weight, however, is easily adsorbed to a polypropylene vessel and so on, which is an injection syringe, and to a glass vessel and so on.

TCF-II is also an unstable substance. The activity of TCF-II is considerably decreased by temperature or humidity and so on, and inactivated easily. Therefore, manufacturing of the stable pharmaceutical composition is required. Accordingly, the pharmaceutical composition in the present invention is a TCF-II one which contains one or more of proteins and nonionic detergents as adsorption preventors, or one or more of proteins, carbohydrates and aminoacids as stabilizing agents, or moreover the—combination of one or more as adsorption preventors and one or more as stabilizing agents.

Any pharmaceutical form which is a lyophilized, or liquid or powder form can be used as a pharmaceutical composition in the present invention, if the above mentioned adsorption preventors and stabilizing agents were included in the pharmaceutical composition. The active component in the present invention, TCF-II can be produced or purified by the any method. TCF-II which is purified from culture broth of any TCF-II secreting cell, can be also used. TCF-II which is produced by the method of recombinant DNA technology, using *Escherichia Coli*, yeast, mammalian cells such as chinese hamster ovary etc, as hosts, and is purified by various methods, can be also used.

Albumin and gelatin etc, among proteins, and Tween 80 and Tween 20 etc, among nonionic detergents can be used as the adsorption preventor in the present invention.

Albumin and gelatin etc, among proteins; sorbitol, mannitol and xylitol etc, among carbohydrates; glycine and alanine etc, among amino acids can be used as the stabilizing agents in the present invention. The suitable added amounts of proteins as the adsorption preventors are more than 0.1%, preferably 0.1 to 20%, and the suitable added amounts of nonionic detergents are more than 0.001%. preferably 0.001 to 1.0%. The suitable added amounts of protein as stabilizing agents are more than 0.1%, preferably 0.1 to 20.0%; the suitable added amounts of carbohydrates are 5 to 40%; and the suitable added amounts of amino acids are more than 1%. On the case of using with combination of one or more of adsorption preventors and one or more of stabilizing reagents, or using with combination of two or more of stabilizing agents, the added amounts of each agent were permitted in the above mentioned range. The reasonable amounts of these adsorption preventors and stabilizing agents are dissolved and prepared as aqueous solution with suitable concentration and pH which can be used. The ratios of permeability pressure of this solutions are in the range of 0.1 to 3.1, preferentially 1.0. Since the stable range of TCF-II against pH is p116 to 9, the aqueous solution for the preparation of pharmaceutical product is suitable to adjust pH to 6.0 to 9.0.

Then, the adsorption-prevention and stability of TCF-II in the pharmaceutical composition in the present invention is further described in detail as shown in Experiments in the following:

EXPERIMENT 1

Test for Prevention of Adsorption

Human embryonic lung fibroblast, IMR-90 cells (ATCC, CCLI86) were cultured for 7 days in DMEM containing 5% fetal bovine serum. 200 µg of TCF-II which was purified from the culture broth was dissolved in 100 ml of 0.01M phosphate buffer, pH7.0, containing 0.15 M NaCl (PBS). Each 0.5 ml of the TCF-II solution was added to glass tubes and polypropylene tubes. Separately, the solutions containing two-fold, concentration of each added material shown in Table 1a, b and c were prepared with PBS. 0.5 ml of the above solution with each concentration of added material was added to each tubes containing 0.5 ml of the TCF-II solution, and mixed well. The final concentration of TCF-II is 1 µg/ml and the final concentration of each added material is adjusted to concentration described in Table 1a, b and c.

As a control, 0.5 ml of PBS was added to each glass tube or polypropylene tube containing 0.5 ml of the TCF-II solution.

Each test was carried out duplicately, and TCF-II activity was determined after the incubation for 1 hour at 37° C. Experimental values were shown as mean of duplicate incubations.

The activity of TCF-II was determined by cytotoxic activity as following.

A clone L929-18 with high sensitivity to TCF-II, which was obtained by subcloning mouse LS29 (ATCC, CCLI), was used as a target cell.

L929-18 cells were grown to confluence in the Dulbecco's modified eagle medium (DMEM) containing 10% FCS, then harvested by trypsin treatment and by centrifugation. The obtained cells were suspended at a cell density of $6 \times 10^5$ cells/ml in DMEM containing 10% FCS and 1 µg/ml of actinomycin D.

A serially diluted test sample was prepared by repeating dilution of test sample with DMEM which was used in the preparation of the cell suspension. Each 50 µl of a serially diluted test sample was added to each well in 96 well-microplate (Falcon).

50 µl of the cell suspension was inoculated into each well containing a serially diluted test sample and the culture was carried out at 37° C. for 2 days in a $CO_2$ incubator. After the culture, the medium was removed gently and the cells were washed twice with PBS. The viable cells which adhere to each well were fixed and stained by addition of 50 µl of 0.5% crystal violet in the mixture of methanol and water (1:4) to each well. Each well was washed with distilled water and dried, and crystal violet in each well was extracted with Sorenson's buffer (mixture of 6.1 ml of 0.1M dissodium citrate, 3.9 ml of 0.1N HCl, and 10 ml of ethanol). Absorbances of the extracts at 570 nm were determined by a microtiter spectrophotometer.

Unit of TCF-II (u/ml) was defined as the dilution ratio given 50% cell death and the residual cytotoxic activity after the incubation was estimated as the relative activity(%) against the activity (100%) determined immediately after the preparation of test sample.

The results in Table 2,a, b, and c showed that TCF-II was easily adsorbed on surface of glass and polypropylene vessels and the adsorption preventors using in the present invention effectively prevented TCF-II from the adsorption.

TABLE 2

(1) Glass Tube a. Effect of high molecular weight additives on adsorption of TCF-II.

| concentration | added material | | | | |
|---|---|---|---|---|---|
| | human serum albumin(HSA) | low mol.w. gelatin* | gelatin | polyethylene glycol 4000 | dextran40 |
| | residual relative activity (%) | | | | |
| 0 | 8.3 | 8.3 | 8.3 | 8.3 | 8.3 |
| 0.01 | 16.7 | 8.3 | 25.0 | 8.3 | — |
| 0.05 | 25.0 | 8.3 | 37.5 | 8.3 | 8.3 |
| 0.1 | 50.0 | 16.7 | 50.0 | 16.7 | — |
| 0.25 | 100.0 | 16.7 | 100.0 | 16.7 | 8.3 |
| 0.50 | 100.0 | 33.3 | 100.0 | 16.7 | 8.3 |
| 1.00 | 100.0 | 50.0 | 100.0 | 16.7 | 12.5 |
| 2.00 | 100.0 | 100.0 | 100.0 | 33.3 | 12.5 |
| 10.00 | 100.0 | 100.0 | 100.0 | — | 75.0 |
| 20.00 | 100.0 | 100.0 | 100.0 | — | — |

*mean molecular weight = 6,000 (NIPPI Co. Ltd)

b. Effect of non-ionic detergents on adsorption of TCF-II

| concentration (%) | added material | |
|---|---|---|
| | Tween80 | Tween20 |
| | residual relative activity (%) | |
| 0 | 8.3 | 8.3 |
| 0.0001 | 16.7 | 16.7 |
| 0.0005 | 25.0 | 25.0 |
| 0.001 | 50.0 | 50.0 |
| 0.005 | 100.0 | 100.0 |
| 0.01 | 100.0 | 100.0 |
| 0.05 | 100.0 | 100.0 |
| 0.10 | 100.0 | 100.0 |
| 1.00 | 100.0 | 100.0 |

(2) Polypropylene Tube c. Effect of human serum albumin and Tween 80 on adsorption of TCF-II

| concentration (%) | added material human serum albumin (HSA) | concentration (%) | added material Tween 80 |
|---|---|---|---|
| | residual relative activity | | residual relative activity |
| 0 | 25.0 | 0 | 25.0 |
| 0.01 | 50.0 | 0.0001 | 33.3 |
| 0.10 | 75.0 | 0.0005 | 50.0 |
| 0.25 | 100.0 | 0.001 | 75.0 |
| 0.50 | 100.0 | 0.005 | 100.0 |
| 1.00 | 100.0 | 0.01 | 100.0 |
| 2.00 | 100.0 | 0.05 | 100.0 |
| 10.00 | 100.0 | 0.1 | 100.0 |
| 20.00 | 100.0 | 1.0 | 100.0 |

EXPERIMENT 2

Stability Test

Under the conditions which prevented TCF-II from adsorption on surface of glass tube, effect of various kinds of added material on the stability of TCF-II was studied. 120 $\mu$g of purified TCF-II from culture broth of IMR-90 cells was dissolved in 30 ml of PBS containing 0.02% Tween 80. After sterilization by filtrating the TCF-II solution using 0.22$\mu$ filter, 0.5 ml of the sterilized TCF-II solution was added to each sterilized glass tube.

The solution with two-fold concentration of each added material shown in Table 2 a, b and c, was prepared, and then sterilized by filtration with 0.22$\mu$ filter. 0.5 ml of the each solution was added to each glass tube containing 0.5 ml of TCF-II solution and after mixing well, the glass tubes were sealed to prevent bacteria from contamination. As a control, 0.5 ml of PBS not containing Tween 80 was added to each glass tube [] containing 0.5 ml of TCF-II solution. The final concentration of TCF-II, Tween 80 and each added material were 2 $\mu$g/ml, 0.01% and concentration shown in Table 3a,b and c, respectively.

Each test was carried out duplicate. The TCF-II activity was determined after the incubation for one week at 40° C. and estimated as relative activity (%) against the activity (100%) determined before the incubation. Experimental values were shown as mean of duplicate incubations.

From the results of Table 3a, b and c, it was found that stabilizing agents which were used in the present invention had the effect which keeps on maintaining the activity of active component, TCF-II in the liquid state.

TABLE 3 a. Effect of high molecular weight additives on stability of TCF-II*

| | added concentration (% W/V) | storage period (da6) at 40° C. | | |
|---|---|---|---|---|
| | | 0 | 3 | 7 |
| | | residual relative activity (%) | | |
| human serum albumin | 0.0 | 100.0 | 25.0 | 16.7 |
| | 0.1 | 100.0 | 50.0 | 33.3 |
| | 0.25 | 100.0 | 100.0 | 100.0 |
| | 0.5 | 100.0 | 100.0 | 100.0 |
| gelatin | 0.0 | 100.0 | 25.0 | 16.7 |
| | 0.1 | 100.0 | 25.0 | 25.0 |
| | 0.25 | 100.0 | 100.0 | 100.0 |
| | 0.5 | 100.0 | 100.0 | 100.0 |
| low mol. weight gelatin (mean M.W. 6,000) | 0.0 | 100.0 | 25.0 | 16.7 |
| | 0.5 | 100.0 | 25.0 | 16.7 |
| | 2.5 | 100.0 | 33.3 | 25.0 |
| | 0.0 | 100.0 | 25.0 | 16.7 |
| polyethylen-glycol 4000 | 0.5 | 100.0 | 16.7 | 12.5 |
| | 2.5 | 100.0 | 16.7 | 12.5 |

*All test samples contained 0.01% Tween 80 to prevent TCF-II from adsorption on surface of glass tube.

b. Effect of added carbohydrates on stability of TCF-II

| | added concentration (% W/V) | storage period (day) at 40° C. | | |
|---|---|---|---|---|
| | | 0 | 3 | 7 |
| | | residual relative activity (%) | | |
| Dextran40 | 0 | 100.0 | 25.0 | 16.7 |
| | 2 | 100.0 | 25.0 | 8.3 |
| | 10 | 100.0 | 12.5 | 4.2 |
| Sorbitol | 0 | 100.0 | 25.0 | 16.7 |
| | 2 | 100.0 | 33.3 | 25.0 |
| | 10 | 100.0 | 66.7 | 66.7 |
| | 20 | 100.0 | 100.0 | 100.0 |
| | 40 | 100.0 | 100.0 | 100.0 |
| Mannitol | 0 | 100.0 | 25.0 | 16.7 |
| | 2 | 100.0 | 33.3 | 16.7 |
| | 10 | 100.0 | 66.7 | 50.0 |
| | 20 | 100.0 | 100.0 | 95.0 |
| | 40 | 100.0 | 100.0 | 100.0 |
| Glucose | 2 | 100.0 | 16.7 | 8.3 |
| | 10 | 100.0 | 12.5 | 4.2 |
| | 20 | 100.0 | 25.0 | 16.7 |
| Fructose | 2 | 100.0 | 12.5 | 6.3 |
| | 10 | 100.0 | <2.0 | <2.0 |
| Mannose | 0 | 100.0 | 25.0 | 16.7 |
| | 2 | 100.0 | 16.7 | 4.2 |
| | 10 | 100.0 | <2.0 | <2.0 |
| Xylitol | 0 | 100.0 | 25.0 | 16.7 |
| | 2 | 100.0 | 33.3 | 16.7 |
| | 10 | 100.0 | 100.0 | 66.7 |
| | 20 | 100.0 | 100.0 | 96.5 | c. Effect of added amino acids on stability of TCF-II*

| amino acid | added concentration (%) | storage period (day) at 40° C. | | |
|---|---|---|---|---|
| | | 0 | 3 | 7 |
| | | residual relative activity (%) | | |
| Arginine | 0 | 100.0 | 25.0 | 16.7 |
| | 1 | 100.0 | 25.0 | 16.7 |
| | 5 | 100.0 | 50.0 | 33.3 |
| Glycine | 0 | 100.0 | 25.0 | 16.7 |
| | 1 | 100.0 | 33.3 | 25.0 |
| | 5 | 100.0 | 100.0 | 66.7 |
| | 10 | 100.0 | 100.0 | 100.0 |
| Lysine | 0 | 100.0 | 25.0 | 16.7 |
| | 1 | 100.0 | 25.0 | 16.7 |
| | 5 | 100.0 | 66.7 | 16.7 |
| Alanine | 0 | 100.0 | 25.0 | 16.7 |
| | 1 | 100.0 | 25.0 | 16.7 |
| | 5 | 100.0 | 100.0 | 50.0 |
| | 10 | 100.0 | 100.0 | 90.0 |

*All test samples contained 0.01% Tween 80 to prevent TCF-II from adsorption on surface of glass tube.

Nextly, the results of pharmacological activities of TCF-II were shown in the following.

In Vivo Antitumor Test to Sarcoma 180 of Human New Cytokine, TCF-II

Materials and Methods

① Experimental Animals

Female ICR mice of 7 weeks old were purchased from Charles River Japan Inc.

② Tumor Cell Lines

Sarcoma 180 cells were supplied by National Cancer Center, subcultured in mice with one time per week on this laboratory.

③ Test Samples

Test samples were prepared by dissolving TCF-II in 0.01M phosphate buffer, pH7.0 containing 0.8% NaCl, 0.01% Tween 80 and 0.25% human serum albumin.

Two series of test samples composed of 0.2 $\mu$g TCF-II/0.2 ml and 1.0 $\mu$g TCF-II/0.2 ml were prepared. Tolanalize the effect of pyrogen, test sample (940 $\mu$g pyrogen/0.2 ml)

containing standard pyrogen (Difco Inc.) corresponding to the amounts of pyrogen in 1 μg of TCF-II was also prepared.

④ Acute Toxicity Test

Acute toxicity test was carried out, using two mice group. Two doses, 10 μg TCF-II/mouse and 20 μg TCF-II/mouse were administered by injecting them into the tail vein of mice, respectively. Toxicity was determined from mortality of animals.

⑤ Antitumor Test

Antitumor test was carried out, using seven mice/group. Sarcoma 180 ($10^6$ cells/mouse) were planted under the skin of ICR mouse. The mice were divided in each test group and the test samples were injected into the tail vein for 7 days at one time/every day. Inhibitory effect of tumor growth was determined by inhibitory ratio $$\left(\frac{C-T}{C} \times 100\%\right)$$

which was obtained from mean tumor weight (MTW) of injected groups against control group.

Results of Tests

① Acute Toxicity Test

Toxicity was not appeared at doses of both 10 μg and 20 μg TCF-II/mouse.

② Antitumor Test

Results after 3 weeks from the initiation of injection were shown in Table 4.

TABLE 4

| Sample | Dose | MTW (mg) | $\frac{C-T}{C} \times 100(\%)$ |
|---|---|---|---|
| control | 0.0 | 3024.71 | — |
| pyrogen | 940 pg/mouse | 3036.00 | −0.37 |
| TCF-II | 0.2 μg/mouse | 1787.71 | 49.92 |
| TCF-II | 1.0 μg/mouse | 1984.21 | 34.40 |

Since on the above test, the optimum dose of TCF-II was unknown, test was not carried out by fitted doses. However, from these results, it was found that lower dose rather than high dose was much effective.

Moreover, anti-tumor effect by direct injection to intra-tumor were also studied by following method.

Methods:

Sarcoma 180 (1×$10^6$ cells/mouse) were planted under the skin of ICR mouse. The mice in which solid-tumor were vitally settled, were selected after one week of plantation. 0.2 μg of TCF-II was injected for 7 days at one time/every day. When observation was continued for two weeks after the termination of injection, remarkable anti-tumor effect which caused necrosis of tumor site, changing into black was obtained. Moreover, mice in which tumor was disappeared, were observed.

−○−, −●− and −◑− represent absorbance at 280 nm, plasmininogen activator activity and cytotoxic activity to L929-18 cells, respectively.

Figure 2:
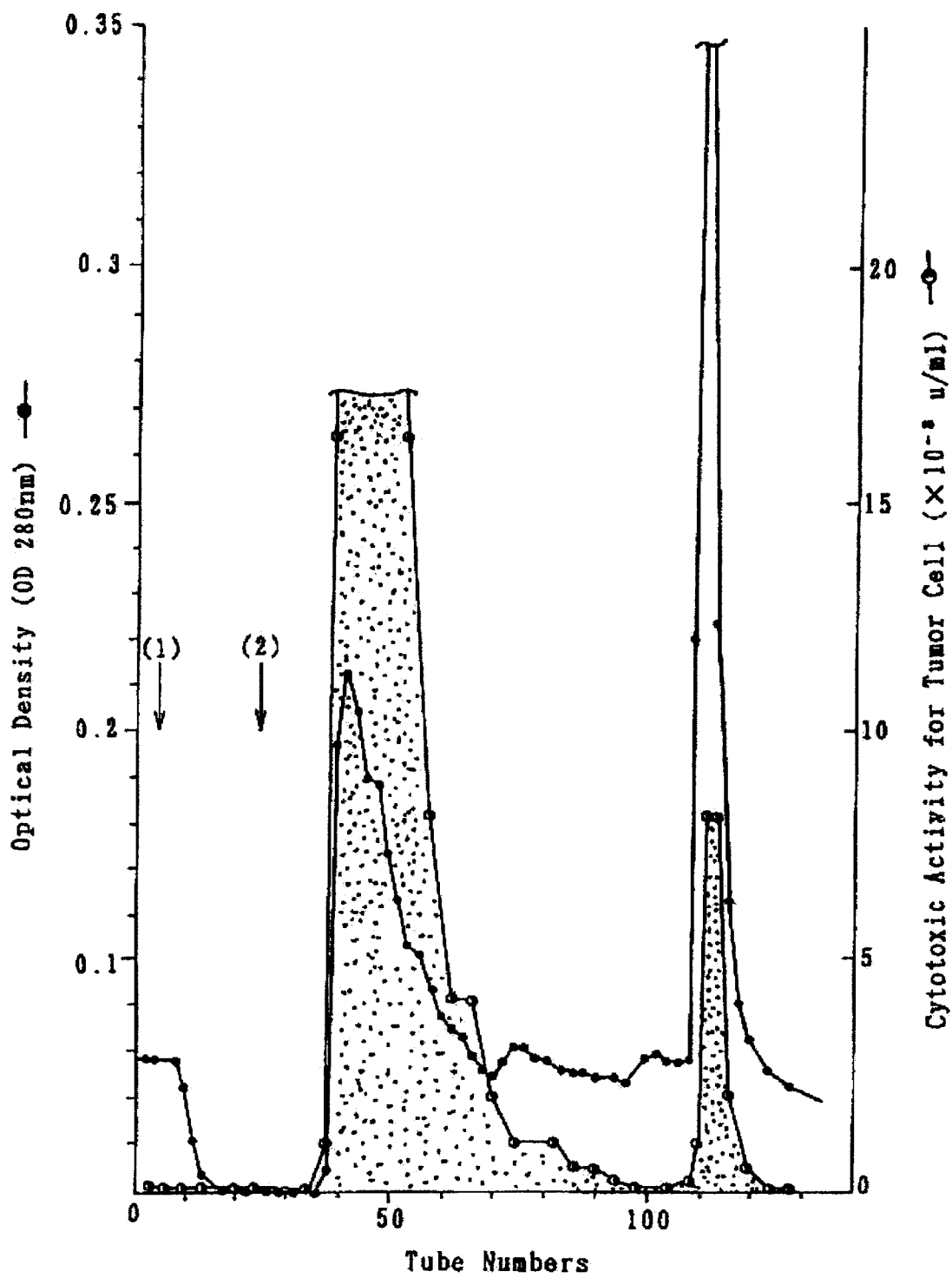

FIG. 2 shows the results of Con A affinity chromatography of TCF-II fraction which was eluted with 0.05M Tris- HCl buffer, pH 7.0, containing 0.6M NaCl on CM-Sephadex C-50 Chromatography of the culture broth of IMR-90 cells. (1) and (2) represent the washed fractions by 0.05M Tris-HCl buffer, pH7.0, containing 0.5M NaCl and the eluted fractions by 0.05M Tris HCl buffer, p17.0, containing. 0.5M NaCl and 0.3M α-methyl-D-mannopyranoside, respectively.

−●− and −◑− represent absorbance at 280 nm and cytotoxic activity, respectively.

Figure 3:
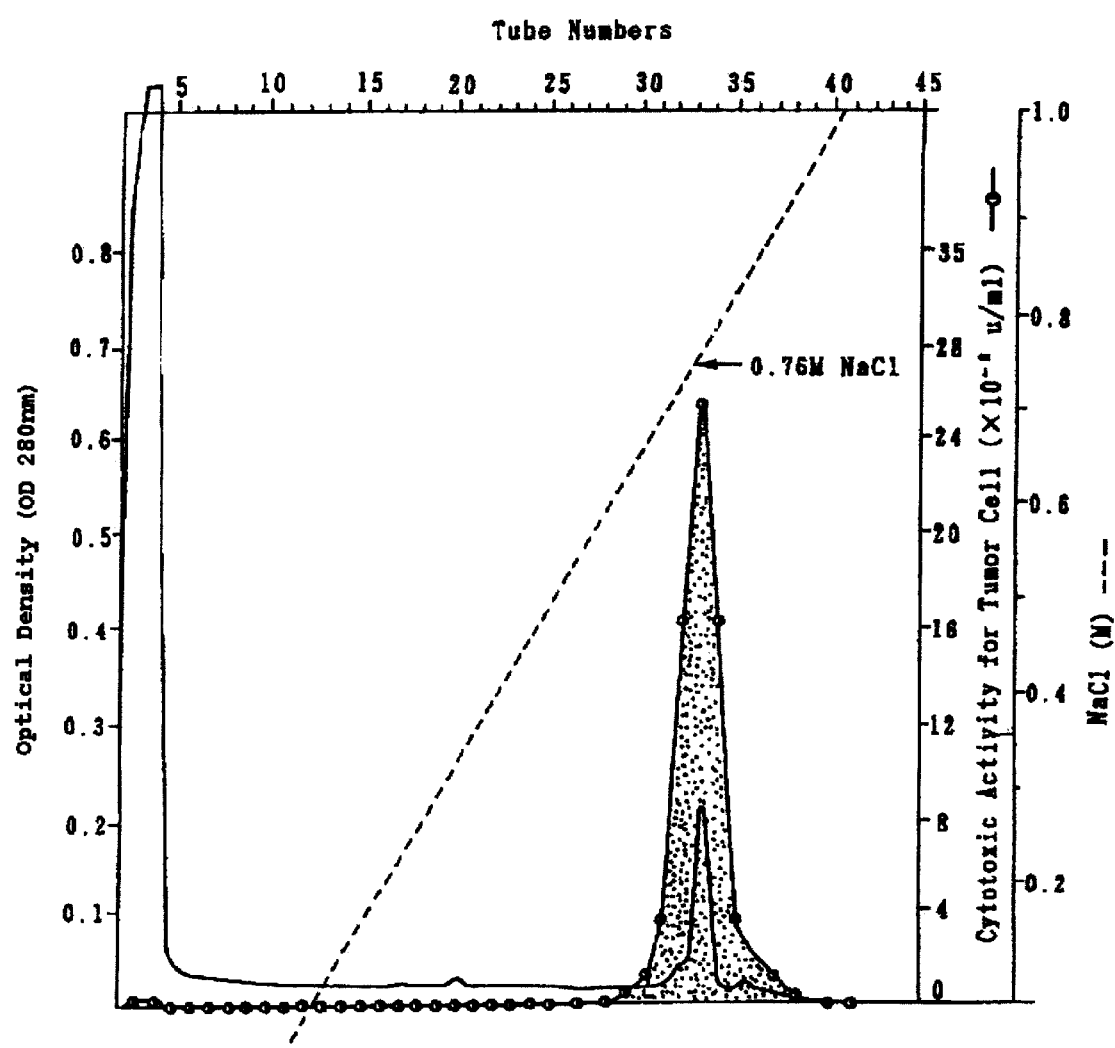

FIG. 3 shows an elution pattern on Mono S-HPLC of the TCF-R fraction which was obtained on Con A Sepharose affinity chromatography. −○− represents cytotoxic activity.

Figure 4:
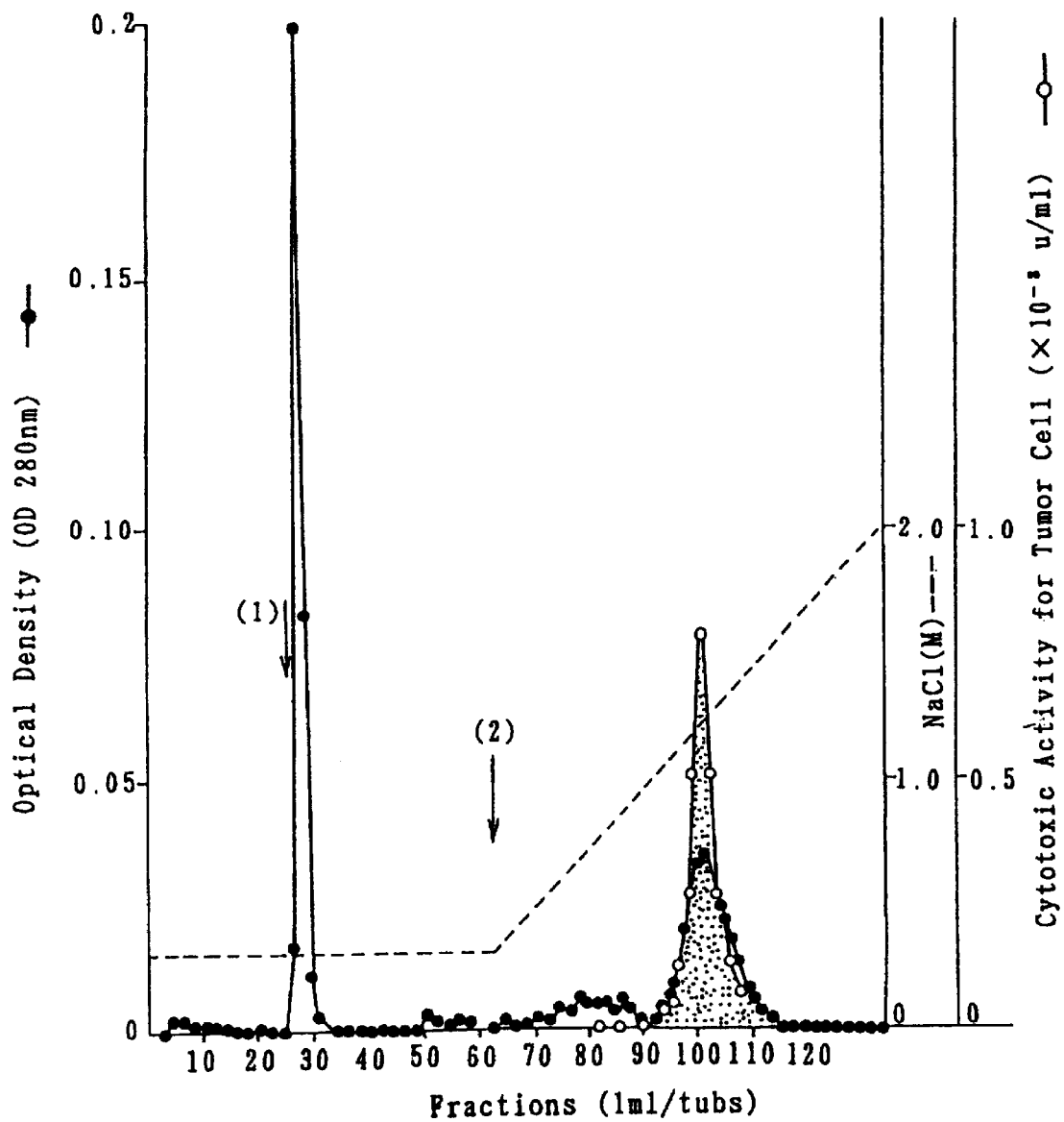

FIG. 4 shows an elution profile of TCF-II on Heparin-sepharose affinity chromatography of the elute from Mono S-HPLC. (1) and (2) represent the washed fraction by 10 mM Tris-HCl buffer, pH7.5, containing 0.3MNaCl and the eluted fraction by NaCl gradient from 0.3 to 2.0M, respectively. −●− and −◑− represent absorbance at 280 nm and cytotoxic activity, respectively.

Figure 5:
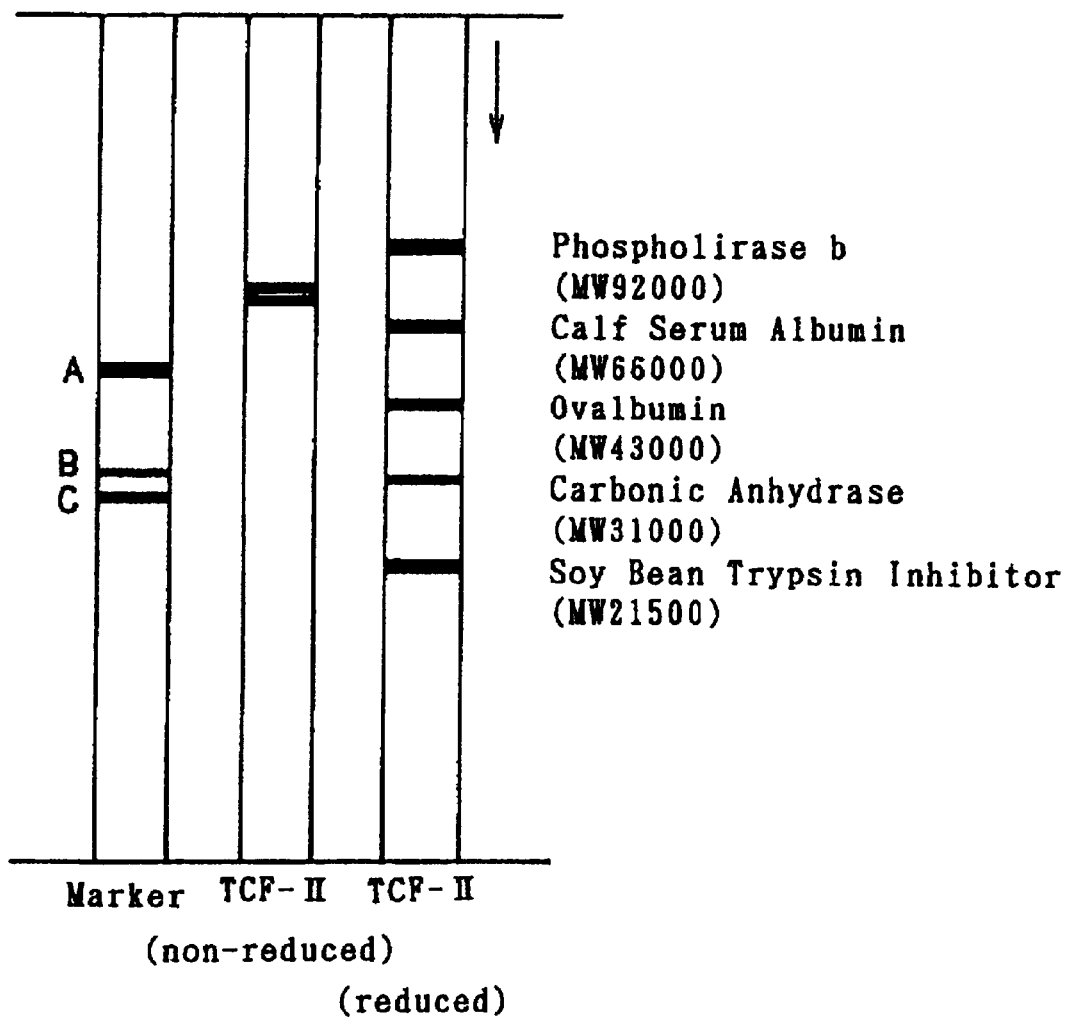

FIG. 5 shows SDS electrophoresis of TCF-II (reduction- and non-reduction).

Figure 6:
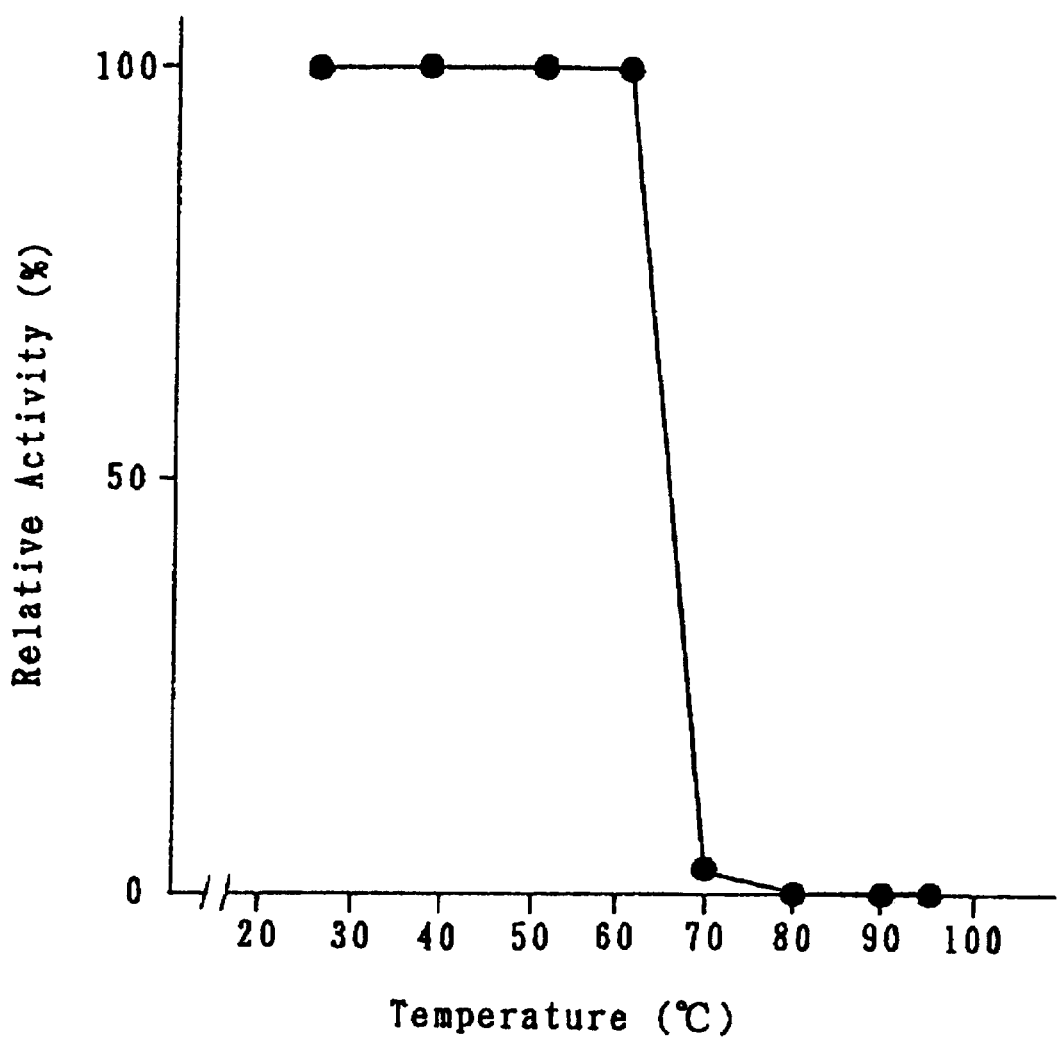

FIG. 6 shows heat stability of TCF-II.

Figure 7:
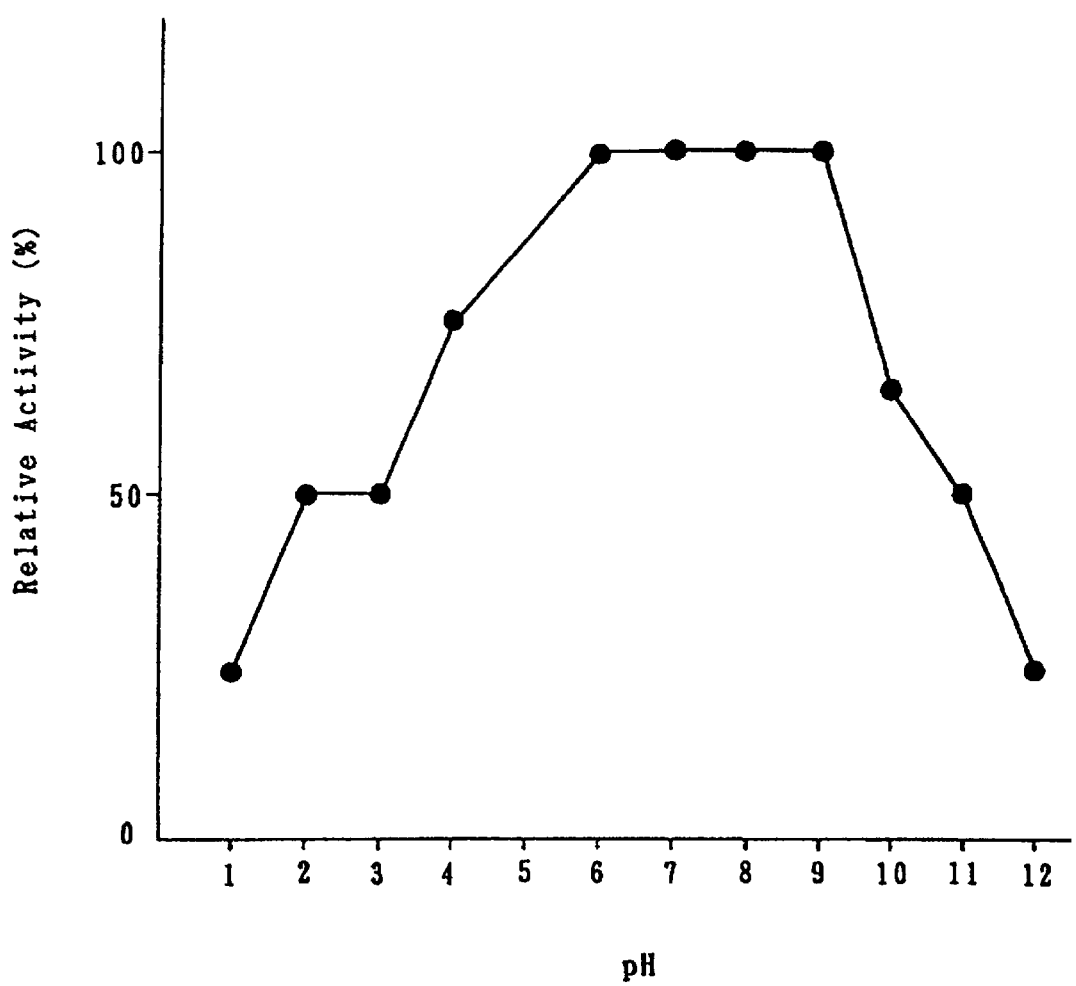

FIG. 7 shows pH stability of TCF-II.

Figure 8:
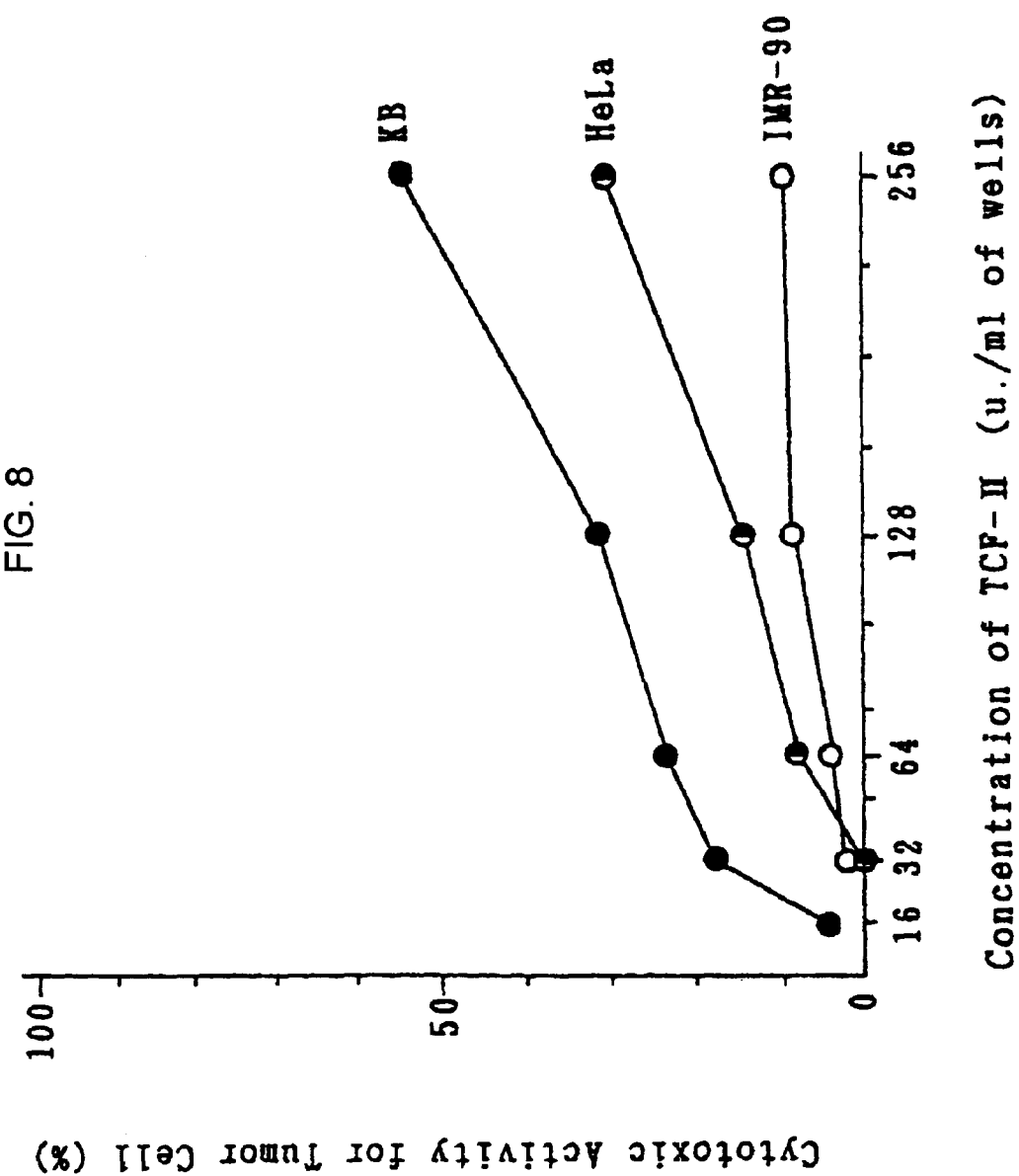

FIG. 8 shows cytotoxic activity of TCF-II to human tumor cell lines in vitro.

Figure 9:
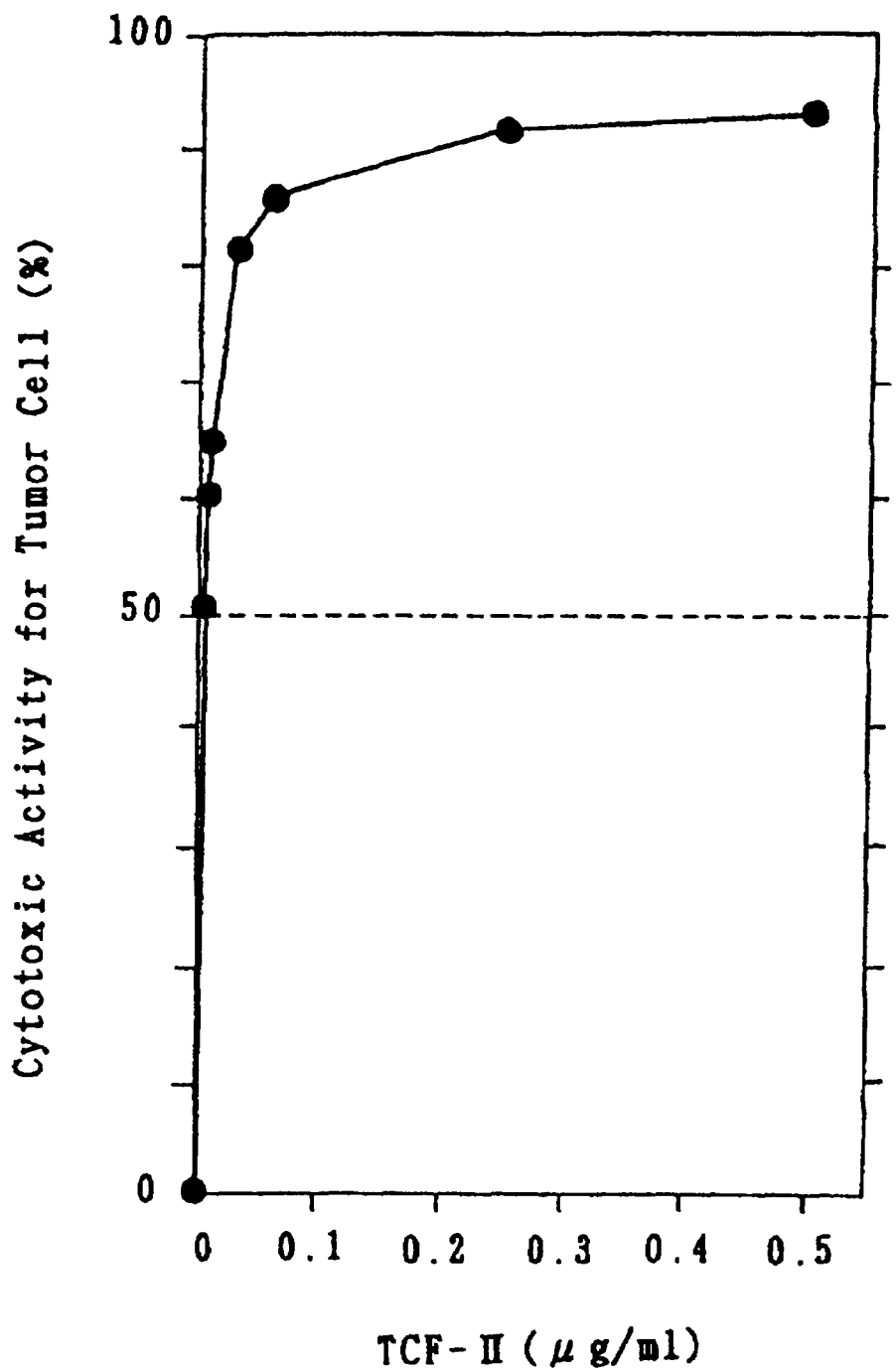

FIG. 9 shows cytotoxic activity of TCF-II to Sarcoma 180.

Figure 10:
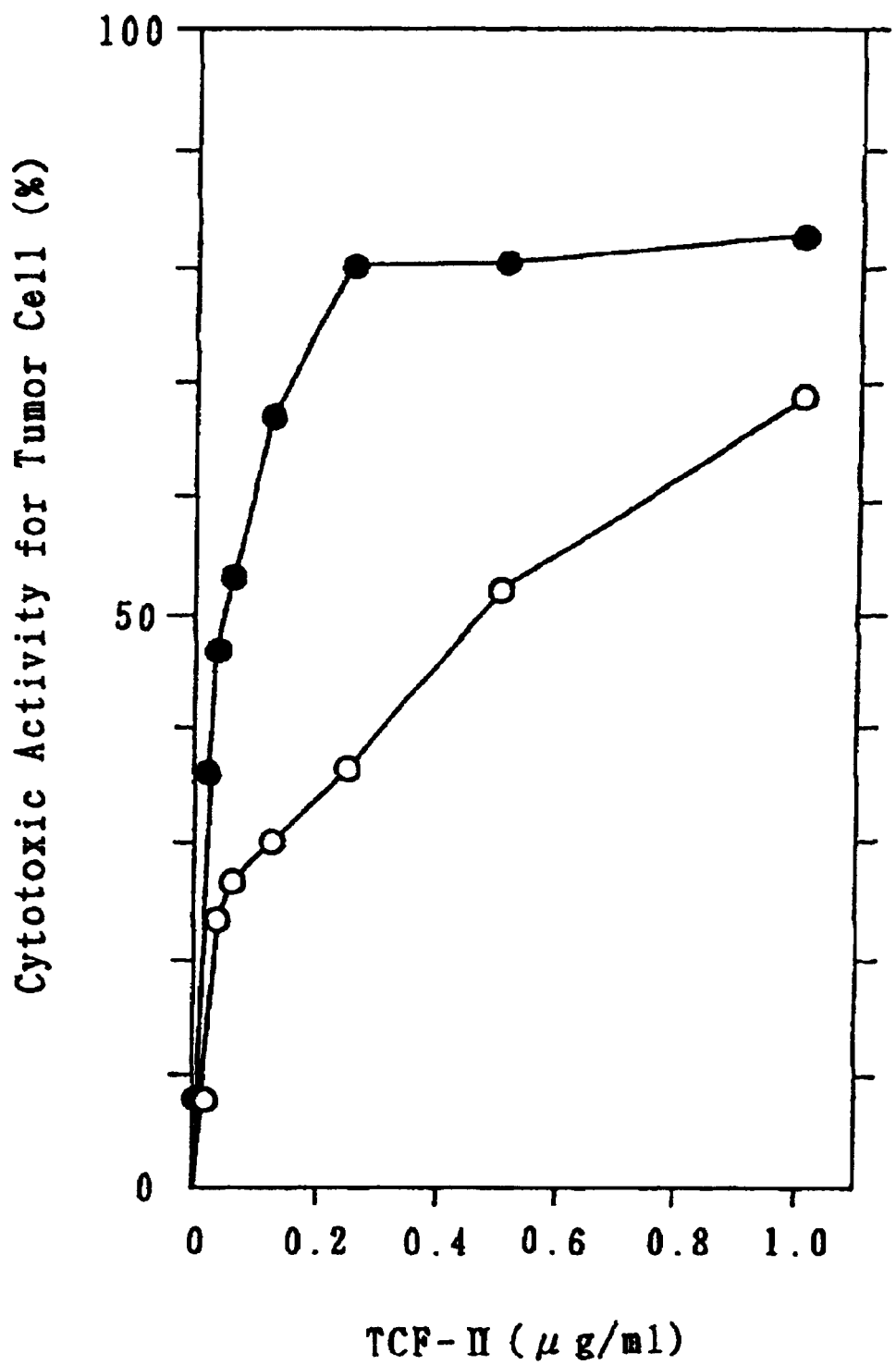

FIG. 10 shows cytotoxic activity of TCF-II to Meth A and P388, respectively. −●− and −◑− represent Meth A and P388. respectively.

Figure 11:
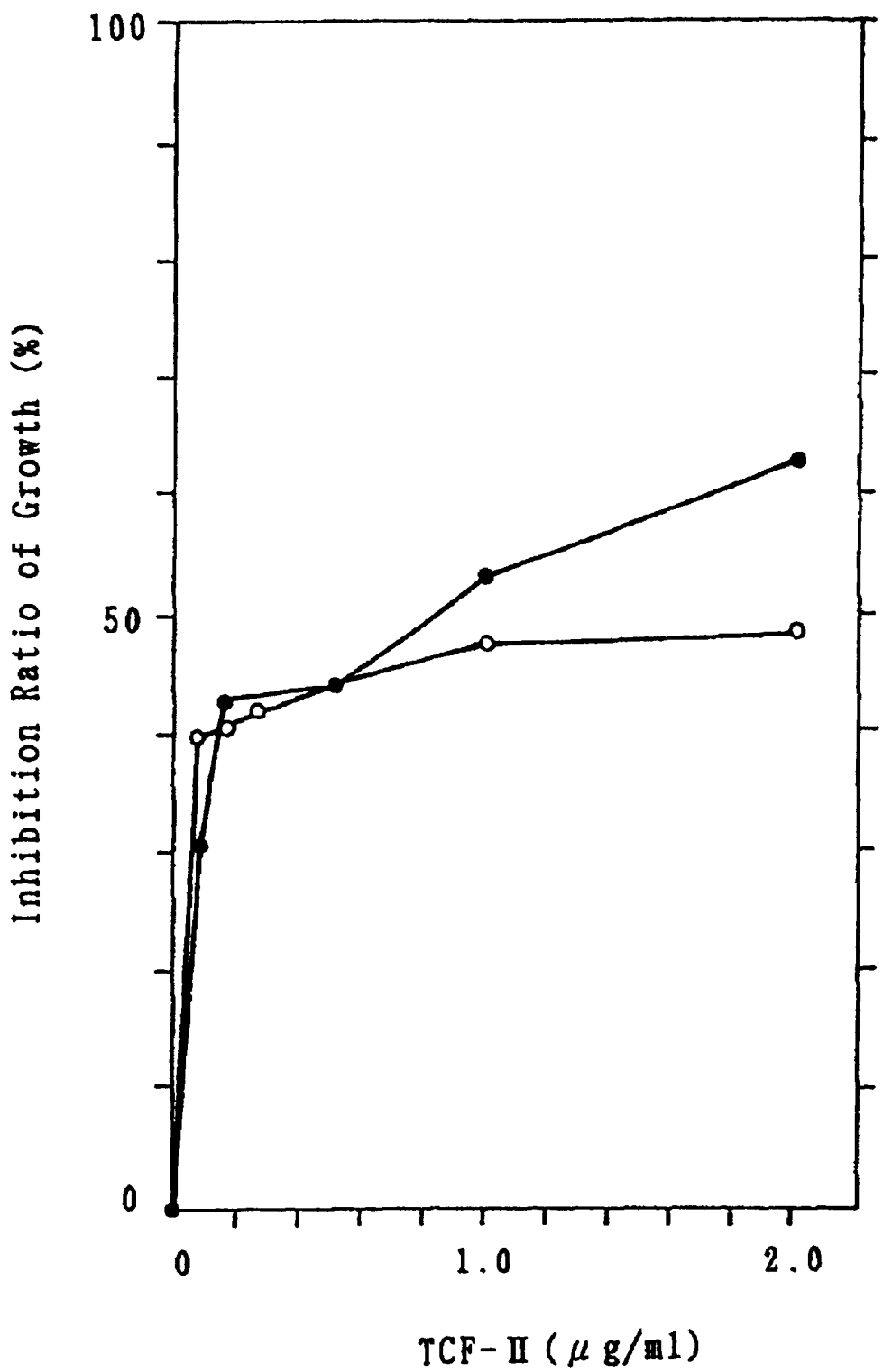

FIG. 11 shows cytostatic activity of TCF-II to human tumor cell lines. −●− and −○− represent cytostatic activities to ovarian carcinoma, BG-1 and breast carcinoma, MCF-7, respectively.

FIG. 12 and FIG. 13 show effect of TCF-II on incorporation of JH-thymidine into the lymphocytes in the mixed lymphocytes culture at day 5 and at day 8, respectively. Six samples at day 5 and at day 8 were determined, respectively. Results are given as mean ±SD.

Figure 14:
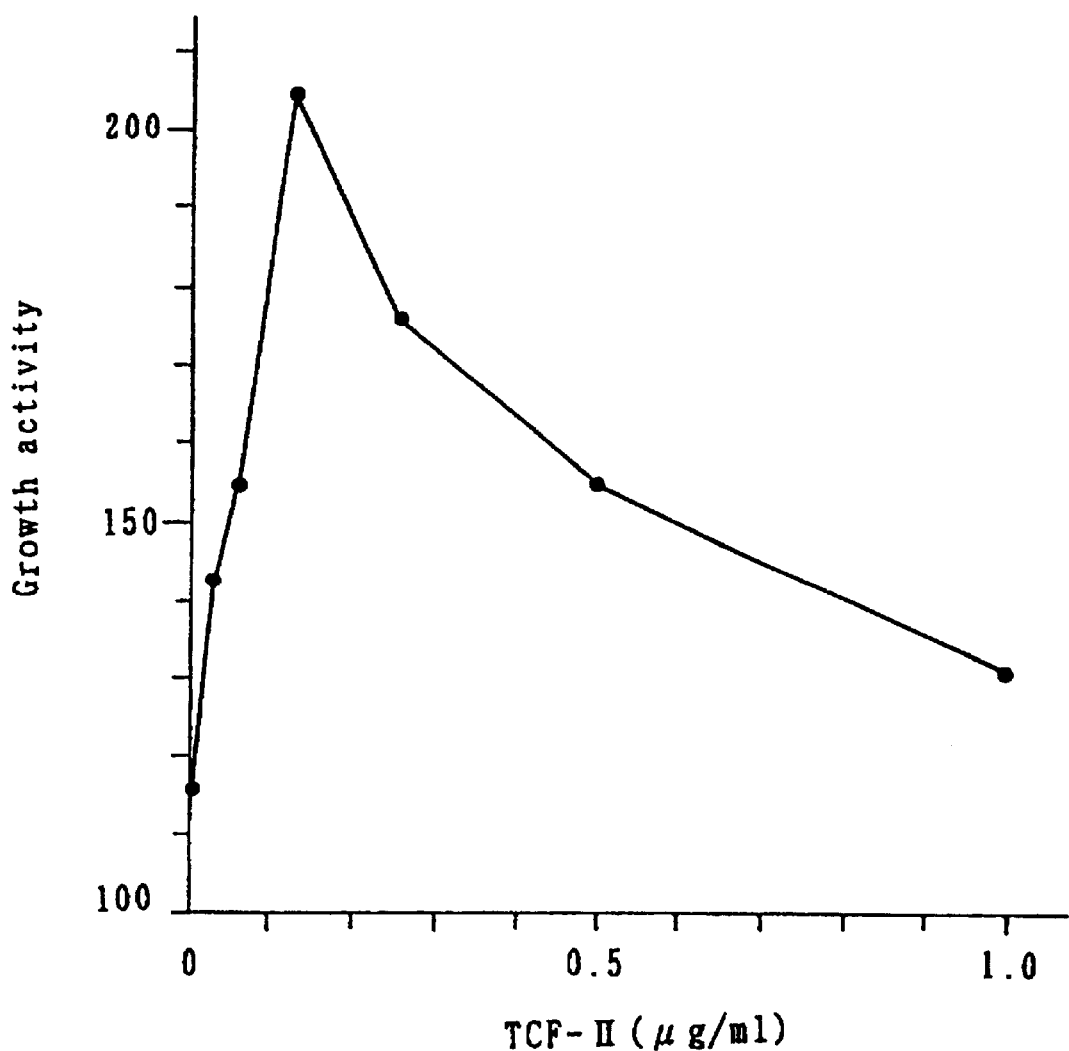

FIG. 14 shows the stimulatory effect of TCF-II on the growth of vascular endothelial cells, HUVEC.

FIGS. 15(1) and (2) show the base sequence of TCF-II cDNA and the amino acid sequence of TCF-II, which was deduced from the base sequence, respectively.

FIG. 16 shows the comparison between the amino acid sequence of TCF-II, which was deduced from the above base sequence and an amino acid sequence of hHGF reported by Miyazawa et al.

BEST MODE OF THE INVENTION

The present invention is further described concretely as shown in EXAMPLES to the following EXAMPLES:

EXAMPLE 1

(1) Culture of Human Fibroblast, IMR-90 cells

Human fibroblast, IMR-90 cells(ATCC CCL 186) (3×$10^6$ cells) were inoculated in one liter-roller bottle holding 100 ml DMEM containing 5% calf serum (CS), and were cultured for 7 days with rolling at the rates off 0.5 to 2 rpm. When the total cell numbers reached 1X $10^7$ cells, the cells were harvested by trypsin treatment and collected in bottom of the bottle. After adding 250 ml of fresh DMEM containing 5% CS to the bottle, 100 g of autoclaved ceramics with 5 to 9 mesh (Toshiba Ceramic. Co. Ltd) was added to the bottle containing cell suspension. Standing culture was carried out at 37° C. for 24 hours. Then 250 ml of DMEM containing 5% CS was added to the bottle (final medium volume was 500 ml), and the culture was continued. Every 7 to 10 days all amount of the medium (about 500 ml) was collected and fresh medium (500 ml) was supplied. Thus, the production was continued for 2 months and 4 l of the culture broth were collected per roller bottle. Specific activity of thus obtained culture broth was 32 u/ml.

Figure 1:
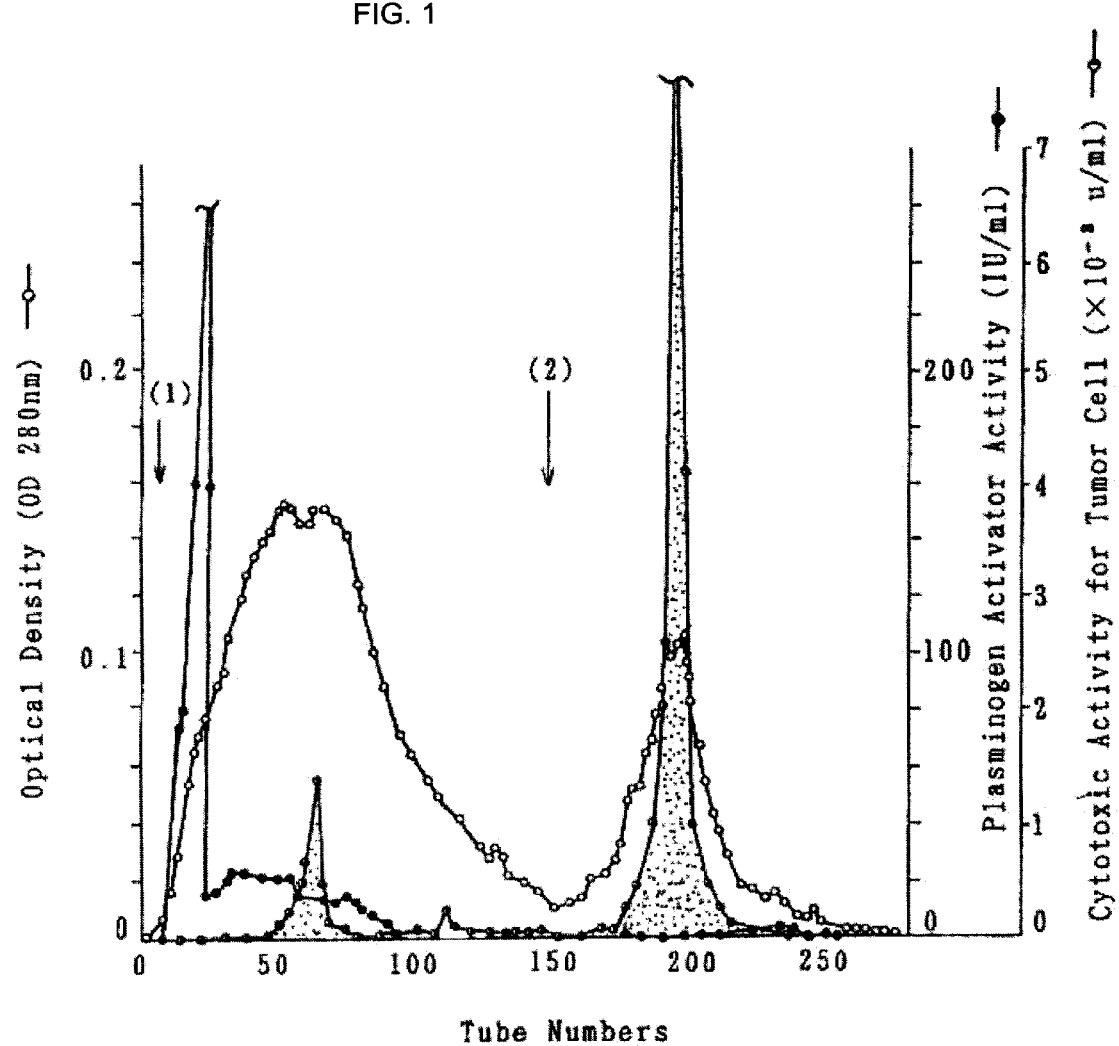
FIG. 1 shows an elution profiles of TCF-II and plasminogen activator from the culture broth of IMR-90 cells containing 5% calf serum on CM-Sephadex C-50 chromatography. (1) and (2) shows the fractions eluted with 0.05M Tris-HCl buffer, pH7.0, containing 0.3M NaCl and with 0.05M Tris-HCl buffer, pH7.0, containing 0.6M NaCl, respectively.

(2) Purification of the Glycoprotein, TCF-II 75 liters of the culture broth described in (1) was concentrated about 10-fold by UF concentration, using Amikon-membrane filter (pore size, M.W. 6,000). Then, after CMSephadex C-50 was equilibrated with 0.05M Tris-HCl buffer, pH7.0, 1.5 kg of wet weight of the resins was added to the above UF concentrated broth and the substance was absorbed to the resins by gently stirring at 4° C. for 24 hour under pH 6.5 to 7.0. After the absorption, the resins were collected by filtrating through a Whatman No. 2 filter paper. The collected resins were washed with 0.05M Tris-HCl buffer, pH7.0. Approximately 1500 g of the washed resins was packed to the column ($\phi$7×40 cm), and the column was eluted with 0.05M Tris-HCl, pH7.0, containing 0.01% Tween 20 and 0.3M NaCl. Elution of protein was monitored by absorbance at 280 nm. When protein was eluted almost completely, further elution at salt concentration of 0.6M NaCl was carried out. Cytotoxic activity to L929-18 cells and tissue plasminogen activator (t-PA) activity which IMR-90 cells produce were determined in each fraction. Thus obtained elution pattern is shown in FIG. 1. The fraction which was eluted at salt concentration of 0.6M NaCl exhibited the potent cytotoxic activity. This fraction was defined as TCF-II fraction. Then, Con A-Sepharose CL-6B (Pharmacia) was equilibrated with 0.05M Tris-HCl buffer, pH7.0, containing 0.5M NaCl, and the gel was packed into the column ($\phi$2.5×8 cm). The column was washed well with the same buffer, the TCF-II fraction which was eluted from the CM-Sephadex column was loaded on the column. After the column was washed again with 0.05M Tris-HCl, pH7.0, containing 0.5M NaCl with 10 times volume of the column bed volume, the substance was eluted with 0.05M Tris-HCl, pH7.0, containing 0.5M NaCl and 0.3M $\alpha$-methyl-D-mannopyranoside at a flow rate of 70 ml/hour. Elution of protein was monitered by optical absorbance at 280 nm and cytotoxic activity in each fraction was determined. Thus obtained elution pattern is shown in FIG. 2. The fraction which was eluted firstly was collected and dialyzed against distilled water for 48 hours. The dialyzed fraction was lyophilized and white powder was obtained. The lyophilized powder was dissolved with a small volume of 0.05M Tris-HCl buffer, pH7.0, containing 0.01% Tween 20 and 0.2M NaCl, and was loaded on MonoS column (Pharmacia) for HPLC which was equilibrated with 0.01M phosphate buffer, pH 7.0, containing 0.01% Tween 20. After the column was washed with 0.1M phosphate buffer, pH7.0, containing 0.01% Tween 20 for 20 min at a flow rate of 0.5ml/min, elutionwas carried out by the Nacl gradient from 0 to 1.0M in 60min. The obtained elution pattern is shown in FIG. 3. The active fraction was eluted at 0.76M NaCl. The active fraction was collected and diluted with the equilibration buffer and then loaded on the Mono S column for HPLC again. Elution was carried out again by the NaCl gradient from 0 to 1.0 M NaCl in the same buffer. Heparin-Sepharose (Pharmacia) was equilibrated with 10 mM Tris buffer, pH 7.0, containing 0.3M NaCl, and 5ml of the gel was packed to the column ($\phi$1.0×7cm). The active fraction from Mono S-HPLC was collected, diluted with 0.01M Tris-HCl buffer, pH7.0, to NaCl concentration of 0.3M, and loaded on the above mentioned column. Then, the column was washed with 0.01M Tris-HCl pH7.0, containing 0.3M NaCl with 10 times volumes of the column bed volume. The substance was eluted at a flow rate of 20 ml/hour by the NaCl gradient from 0.3M to 2.0 M in the same buffer. The elution pattern is shown in FIG. 4. Thus, the purified glycoprotein was obtained. As shown in Table 5, 0.12 mg of the active glycoprotein was obtained from 75 liters of the culture broth as the starting material. This glycoprotein was a tumor cytotoxic factor and its specific activity was 5,248,000 u/mg.

TABLE 5

Purification of tumor cytotoxic factor obtained from the culture broth of IMR-90 (containing 5% CS)
TCF-II:A fraction eluted with 0.6M NaCl on Sephadex C-50 chromatography

| Purification Step | Volume (ml) | Protein (mg/ml) | Total Protein (mg) | Cytotoxic Activity (u/ml) |
| --- | --- | --- | --- | --- |
| Culture broth | 75000 | 3.30 | 247500.0 | 32.0 |
| UF Concentration | 10000 | 23.40 | 234000.0 | 192.0 |
| CM-Sephadex chromatography (eluted fraction with 0.6M NaCl) | 894 | 0.32 | 205.6 | 2048.0 |
| ConA Sepharose chromatography | 244 | 0.26 | 63.4 | 5120.0 |
| Mono S-HPLC | 13 | 0.26 | 2.1 | 80000.0 |
| Heparin-Sepharose chromatorgraphy | 6 | 0.02 | 0.12 | 104960.0 |

| Total Activity ($\times 10^4$u) | Specific Activity (u.mg) | Purification Factor | Recovery (%) |
| --- | --- | --- | --- |
| 24.0 | 9.7 | 1.0 | 100.0 |
| 192.0 | 8.2 | 0.9 | 80.0 |
| 183.1 | 8904.3 | 918.0 | 76.3 |
| 124.9 | 19692.3 | 2030.0 | 52.0 |
| 104.0 | 500000.0 | 51546.4 | 43.3 |
| 56.0 | 5248000.0 | 541030.9 | 23.3 |

Physicochemical properties of TCF-II obtained by the above mentioned procedure are shown as follows.

① Determination of Molecular Weight on SDS Gel Electrophoresis

Molecular weight of TCF-II was determined by electrophoresis using polyacrylamide gel containing 0.1% SDS. The glycoprotein showed two adjucent bands with M.W. 78,000 and 74,000. When the glycoprotein was reduced by 2-mercaptoethanol and the similar electrophoresis was carried out, three bands with molecular weight of 52,000, 32,000, and 28,000 were observed (FIG. 5).

These results indicate that TCF-II is a heterodimer composed of a common subunit with M.W. 52,000 and a subunit of M.W. 28,000 or a subunit of M.W. 32,000.

② Isoelectric point

Isoelectric point of the substance was determined as 7.4 to 8.55 by isoelectric focussing, using Phast Gel IEF3-9.

③ Bleat Stability

TCF-II which had the activity of 51,200 u/ml was added to 0.1M Tris-HCl buffer, pH7.0, containing 0.01% Tween 20 and the TCF-II solution with 512 u/ml was prepared. The solution was treated for 10 min at 25, 35, 50, 60, 70 80, 90, and 95° C. The residual cytotoxic activity (u/ml) after treatment at each temperature was estimated as the relative activity (%) against the activity (u/ml, 100%) at 25° C. (control). As shown in FIG. 6, the substance was stable till 60° C.

④ pH stability

Each buffer containing 0.01% Tween 20, composition of which was shown in Table 6, was prepared. The amount of TCF-II corresponding to 51,200 u/ml when it was prepared at pH 8 was dissolved in each buffer, and allowed to stand at 37° C. for 1 hour. The relative activity (%) compared to the control at room temperature for one hour was determined. As shown in FIG. 7, the glycoprotein was stable in the range of pH6 to 9.

TABLE 6

| Preparation of buffers | |
|---|---|
| pH1–3 | 1/10 M Glycine-HCl |
| pH4–6 | 1/10 M Acetate buffer |
| pH7–8 | 1/10 M Tris-HCl |
| pH9.12 | 1/10 M Glycine-NaOH |

⑤ N-terminal amino acid sequence of TCF-II

50 μg of TCF-II was reduced and three polypeptides, A with M.W. 52,000, B with M.W.32,000, and C with M.W. 28,000, were separated by the electroblot method. Amino acid sequence of each polypeptide was analyzed using the Applied Biosystems 477A Protein Sequencer. N-terminal amino acid sequence of polypeptide A could not be determined because its N-terminus had been blocked. Polypeptides B and C had the common N-terminal amino acid sequence as follows;

```
Val-Val-Asn-Gly-Ile-Pro-Thr-X-Thr-Asn-Ile-Gly-
 1   2   3   4   5   6   7  8  9   10  11  12

X-Met-Val-Ser-Leu-
13  14  15  16  17
```

X means an unidentified amino acid.

Since polypeptide B and C show the same N-terminal amino acid sequence, TCF-II appears to have dimer structure in which polypeptide A with M.W. 52,000 is bound to polypeptide B with M.W. 32,000 or to polypeptide C with M.W. 28,000 by S-S bridge.

⑥ Amino acid composition

Ten μg of TCF-II. which was determined by BioRad Protein Assay kit, was hydrolyzed with HCl and then its amino acid composition was determined using a Hitachi Amino Acid analyzer, Model L-8500.

Amino acid composition of the material is shown as follows.

Amino acid composition:

| A.A | nmol | mol % |
|---|---|---|
| Asp | 10.375 | 12.97 |
| Glu | 7.750 | 9.69 |
| Ser | 5.000 | 6.25 |
| Gly | 7.250 | 9.06 |
| His | 3.000 | 3.75 |
| Arg | 5.375 | 6.72 |
| Thr | 5.125 | 6.41 |
| Ala | 2.625 | 3.28 |
| Pro | 5.625 | 7.03 |
| Tyr | 3.875 | 4.84 |
| Val | 4.125 | 5.16 |
| Met | 1.875 | 2.34 |
| Cys | ND | — |
| Ile | 5.000 | 6.25 |
| Leu | 4.875 | 6.09 |
| Phe | 2.250 | 2.81 |

-continued

| A.A | nmol | mol % |
|---|---|---|
| Trp | ND | — |
| Lys | 5.875 | 7.34 |
| total | 80.000 | 100(99.99) |

EXPERIMENT 2

Cytotoxic activity to the tumor cells of the glycoprotein, TCF-II obtained in EXPERIMENT 1 is shown.

① Inhibition of the Growth of Tumor Cells

The human tumor cell lines, HeLa and KB, and the human normal diploid cells, IMR-90 were suspended at a cell density of $1 \times 10^5$ cells/ml in DMEM containing 10% FCS, respectively. 50 μof each cell suspension was added to each well in a 96 well microplate (Falcon). Each 50 μl of 10-, 20-, 40-, 80- and 160- fold dilution of TCF-II solution (5, 120 u/ml)with DMEM was added to each well containing each cell suspension, and the mixture was cultured at 37° C. for 3 days in a $CO_2$ incubator. The surviving cells in each well were fixed and stained by addition of 50 μl of 0.5% crystal violet solution in the mixture of methanol and water (1:4) to each well. Each well was washed with distilled water and dried, and the crystal violet in each well was extracted with Serenson's buffer. Absorbances of the extracts at 570 nm were determined by a microtiter spectrophotometer.

Cell growth inhibition (%) of TCF-II was calculated compared to the group in the absence of TCF-II as the control, and plotted against the concentration of TCF-II. As shown in FIG. 8, TCF-II showed the potent inhibition of the growth of KB and HeLa cells whereas it did not inhibit the growth of normal cells, IMR-90.

② Reaction with Antibodies for the Known Materials

TCF-II was dissolved in DMEM containing in DMEM containing 10% FCS to the concentration of 320 u/ml. The titer of anti-LT antibody which neutralized 1000 u/ml LT was added to the TCF-II solution and the mixture was allowed to stand at 37° C. for 1 hour. Similarly, anti-TNF antibody and anti-INF-β were added to the TCF-II solution at the concentrations of $1 \times 10^6$ u/ml and 1000 u/ml, respectively. Each antibody used in this experiment is commercialy available.

After the reactions, cytotoxic activity of TCF-II was determined. Any antibody, however, did not neutralize the activity.

EXPERIMENT 3

Cytotoxic activity to various mouse tumor cell lines of the glycoprotein, TCF-II obtained in EXPERIMENT 1 is shown.

Sarcoma 180, Meth A sarcoma and P-388 cells were used as mouse tumor cell lines.

Sarcoma 180 cells were suspended in DMEM containing 10% fetal bovine serum and Meth A and P-388 cells were suspended at $2 \times 10^4$ cells/ml, in RPMI 1640 medium containing 10% fetal bovine serum,respectively. 50 μl of each cell suspension was inoculated into each well in 96-well microplate (Falcon). TCF-II was dissolved in DMEM containing 10% fetal bovine serum for Sarcoma 180 cells and in RPMI 1640 medium containing 10% fetal bovine serum for Meth A and P-388 cells. Each 50 μl of TCF-II solution which was prepared so that the final concentrations of TCF-II were 0, 2, 4, 8. 16, 31, 62, 125, 250, 500 and 1000 ng/ml, respectively, was added to each well containing each cell suspension. After each cell line were cultured at 37° C. for 3 days in a $CO_2$ incubator. The cells in each well were stained with Trypane blue and the viable cell number were counted using a heamacytometer. The viable cell numbers were expressed as mean of duplicate experiments. Cytotoxic activity (%) was calculated according to the following equation.

$$\text{Cytotoxic activity (\%)} = \frac{\text{Average surviving numbers in control (cells/ml)} - \text{Average surviving cell numbers in TCF-II group (cells/ml)}}{\text{Average surviving cell numbers in control (cells/ml)}} \times 100$$

Cytotoxic activities of TCF-II to Sarcoma 180 cells and to Meth A sarcoma and P-388 cells were shown in FIG. 9 and FIG. 10, respectively.

All cell lines were highly sensitive to TCF-II, and the $IC_{50}$ values for cytotoxic activity of TCF-II on Sarcoma 180, Meth A and P-388 cells were 6, 40 and 460 ng/ml, respectively.

EXPERIMENT 4

Inhibitory effect of the glycoprotein, TCF-II obtained in Experiment 1 on human tumor cell lines, ovalian carcinoma, BG-1 and breast carcinoma, MCF-7 is shown in the following.

BG-1 and MCF-7 cells were suspended in McCoy medium containing 10% FCS and in Eagle's MEM containing 10% FCS, non-essential amino acid mixture, pyruvate and Eagle's salts at $2 \times 10^4$ cells/ml, respectively. TCF-II was dissolved in McCoy medium containing 10% FCS for BG-1 cells and in Eagle's MEM containing 10% FCS for MCF-7 and a serially diluted TCF-II solution was prepared by repeating 2-fold dilution of 4 µg TCF-II/ml with the same medium. 50 µl of each cell suspension was inoculated into each well in 96-well microplate (Falcon). Each 50 µl of a serially diluted solution of TCF-II which was prepared for each cell line was added to the wells containing each cell suspension. The culture was carried out at 37° C. for 5 days in $CO_2$ incubator. After the culture, the culture broth was removed and the cells were gently washed twice with PBS. The surviving cells which adhered to each well were fixed and stained by addition of 50 µl of 0.5% crystal violet solution in the mixture of methanol and water (1:4) to each well. Each well was washed with distilled water and dried, and crystal violet in each well was extracted with Serenson's buffer. Absorbances of the extracts at 570 nm were determined by a microtiter spectrophotometer. Cell growth inhibition (%) was calculated for each cell line acc ording to the following equation compared to the control in the absence of TCF-II.

$$\text{Cell growth inhibition (\%)} = \frac{\text{Control OD570 nm} - \text{TCF-II group OD570 nm}}{\text{Control OD570 nm}} \times 100$$

Results are shown in FIG. 11. These results indicate that TCF-II inhibits the growth of both tumor cell lines, BG-1 and MCF-7.

EXPERIMENT 5

Promyelocytic leukemia cell line, HL-60 cells differentiation inducing activity of the glycoprotein, TCF-II obtained in EXPERIMENT 1 is shown.

HL-60 cells were suspended at a cell density of $3.5 \times 10^5$ cells/ml in RPMI 1640 medium containing 10% fetal bovine serum. 100 µl of the cell suspension was added to each well in 96-well flat bottomed microplate(Falcon). Then, 100 µl of the TCF-II solution in the same medium was added to each well containing cell suspension to give the final concentrations of 15.6. 62.5,125, 250, 500, and 1000 ng/ml.

The cells were cultured at 37° C. for 3 and 7 days, and HL-6 cells-differentiation inducing activity of TCF-II was determined by nitroblue tetrazolium (NBT) reduction assay. Moreover, morphological change of the cells was observed.

1) NBT Reducing Ability

NBT reducing ability is shown in Table 7.

TABLE 7

| TCF-II concentration | NBT reducing ability (%) Culture days | |
|---|---|---|
| (ng/ml) | 3 | 7 |
| 0 | 7.4 | 11.7 |
| 15.6 | 10.6 | 20.4 |
| 62.5 | 11.1 | 24.5 |
| 125 | 12.4 | 28.3 |
| 250 | 16.9 | 45.2 |
| 500 | 12.4 | 29.6 |
| 1000 | 12.1 | 26.8 |

The values shown in Table 7 represent percentage of cells containing blue-black formazan deposits (average of 2 experiments) when at least more than 200 cells were counted.

(When HL-60 cells differentiate to normal cells, they get NBT reducing ability and accumulate blue-black formazan in them)

This result has demonstrated that TCF-II induces the differentiation of promyelocytic leukemia cell line, HL-60 and has the highst activity for the differentiation induction at 250 ng/ml.

2) Morphological Change

It is known that HL-60 differentiates to two way of macrophages and granulocytes by differentiation inducing factors.

Changes in morphology and nucleus of the cells which were cultured with TCF-II at 37° C. for 7 days were investigated by the light Giemsa staining method. The result indicates that HL-60 differentiates to granulocyte-like cells.

EXPERIMENT 6

Stimulatory effect on cellular immunology of the glycoprotein, TCF-II obtained in EXPERIMENT 1 is shown.

The effect of TCF-II on blastgenic transformation of lymphocytes was observed when mixed lymphocyte culture was carried out in the presence of TCF-II.

Lymphocytes were isolated from human peripheral blood by the method of Ficall-Conray and suspended in RPMI 1640 containing 10% FCSI. Lymphocytes from two persons were mixed as 1:1 and added to wells in 96 well round bottomed microplate at $1 \times 10^5$ cells/100 µl/well. TCF-II was added at various concentrations and the cells were cultured in RPMI 1640 containing 10% FCS in a $CO_2$ incubator. $^3$H-Thymidine was added at 0.25 g Ci/well at 16 hours before the end of culture. After the culture the cells were harvested by a cell harvester and washed with PBS. The radioactivity of $^3$H-Thymidine incorporated into the cells were determined by a scintillation counter.

Results are given in FIG. 12 and FIG. 13. TCF-II did not show the stimulatory effect at day 5 of the culture as shown in FIG. 12, but $^3$H-thymidine incorporation was significantly stimulated by the presence of TCF-II compared to the control at day 8 as shown in FIG. 13. These results indicate that TCF-II stimulates the growth of cytotoxic T cell, that is, TCF-II possesses the enhancing effect on cellular immunology.

EXPERIMENT 7

Stimulatory effect on vascular endothelial cell growth of the glycoprotein, TCF-II obtained in EXPERIMENT 1 is shown.

Human umbilical vein endothelial cells, HUVEC was used as a test cell. The endothelial cells, HUVEC, were suspended at a cell density of $2.5 \times 10^4$ cells/ml in E-GM medium containing 2% fetal bovine serum. 50 μl of the cell suspension was added to each well in a 96-well flat bottmed microplate (Falcon). Then. 50 μl of the TCF-II solution which was prepared in the same medium was added to give the final concentrations of 0, 4, 8, 16, 31, 62, 125, 250, 500 and 1000 ng/ml. The cells were cultured at 37° C. for 6 days in a $CO_2$ incubator. After the culture, the culture medium in each well was removed and the cells were washed gently with PBS. The cells were removed from the well by trypsin treatment and viable cell numbers were counted using a heamacytometer.

The effect of TCF-II on human normal vascular endothelial cells is shown in FIG. 14. The result indicates that TCF-II does not show the cytotoxic activity to the normal cells but has the stimulatory effect on the growth. Especially, the cell growth stimulatory activity was the maximal at a concentration of 125 μg/ml.

The following Experiments show prescriptions of the pharmaceutical product in the present invention.

| EXPERIMENT 8 | |
|---|---|
| TCF-II | 20 μg |
| Human serum albumin | 100 mg |

The above mentioned compositions were dissolved in 0.01M phosphate buffer, pH7.0, containing 0.15M NaCl (PBS) and the resulted solution was filled up to 20 ml with PBS. After sterilization by filtrating the obtained solution using 0.22μ filter, 2ml of the sterilized solution was poured into each vial tube and lyophilized, and then the vial tubes were sealed.

| EXPERIMENT 9 | |
|---|---|
| TCF-II | 40 μg |
| Tween 80 | 1 mg |
| Human serum albumin | 50 mg |

The above mentioned compositions were dissolved in physiological salt solution (0.8%NaCl) and the solution was increased 20 ml with the same solvent. After the sterilization by filtrating the solution using 0.22μ filter, 2 ml of the sterilized solution was poured into each vial tube and lyophilized, and then the vial tubes were sealed.

| EXPERIMENT 10 | |
|---|---|
| TCF-II | 20 μg |
| Tween 80 | 2 mg |
| Sorbitol | 4 g |

The above mentioned compositions were dissolved in PBS, and the resulting solution was increased 20 ml with PBS. After sterilization by filtrating the solution using 0.22μ filter, 2 ml of the sterilized solution was poured into each vial tube and lyophilized, and then the vial tubes were sealed.

| EXPERIMENT 11 | |
|---|---|
| TCF-II | 40 μg |
| Tween 80 | 2 mg |
| Glycine | 2 g |

The above mentioned compositions were dissolved in physiological salt solution (0.8%NaCl), and the resulting solution was filled up to 20 ml with the same solvent. After sterilization by filtrating the solution using 0.22μ filter, 2 ml of the sterilized solution was poured into each vial tube and lyophilized, and then the vial tubes were sealed.

| EXPERIMENT 12 | |
|---|---|
| TCF-II | 40 μg |
| Tween 80 | 1 mg |
| Sorbitol | 2 g |
| Glycine | 1 g |

The above mentioned compositions were dissolved in physiological salt solution (0.8%NaCl), and the resulting solution was increased 20 ml with the same solvent. After sterilization by filtrating the solution using 0.22μ filter, 2 ml of the sterilized solution was poured into each vial tube and lyophilized, and then the vial tubes were sealed.

| EXPERIMENT 13 | |
|---|---|
| TCF-II | 20 μg |
| Sorbitol | 4 g |
| Human serum albumin | 50 mg |

The above mentioned compositions were dissolved in PBS and the resulted solution was filled up to 20 ml with PBS. After sterilization by filtrating the solution using 0.22μ filter, 2 ml of the sterilized solution was poured into each vial tube and lyophilized, and then the vial tubes were sealed.

| EXPERIMENT 14 | |
|---|---|
| TCF-II | 40 μg |
| Glycine | 2 g |
| Human serum albumin | 50 mg |

The above mentioned compositions were dissolved in physiological salt solution (0.8%NaCl), and the resulting solution was increased 20 ml with the same solvent. After sterilization by filtrating the solution using 0.22μ filter, 2 ml of the sterilized solution was poured into each vial tube and lyophilized, and then the vial tubes were sealed.

Industrial Availability

The present invention provides a new glycoprotein. The glycoprotein in the present invention can be used as a tumor cytotoxic factor, leukemia cell line-differentiation inducing factor, cellular immunology enhancing factor and vascular endothelial cell growth factor and so on, and can be provided usually.

Moreover, the glycoprotein tn the present invention can be used as a biochemical or pharmacological reagent.

What is claimed is:

1. An isolated and purified glycoprotein obtained from the culture broth of human derived fibroblasts and which has the following physicochemical properties,
    a. Molecular weight ranges; On the determinations of molecular weight by SDS gel electrophoresis, 76,000–80,000 or 72,000–76,000 under the non-reduced conditions and a common band A with 50,000–54,000 and band B with 28,000–32,000 or band C with 24,000–28,000 under the reduced conditions;
    b. Isoelectric point; 7.4 to 8.6;
    c. Heat stability; Stable in heating at 60° C. for 10 min;
    d. pH stability; Stable in the range of pH6 to 9;
    e. Carbohydrate chain; Adsorbed to a Concanavalin A (Con A)-Sepharose column;
    f. Biological activity; Inhibits the growth of KB cells, Hela cells, and L-929 cells but not IMR-90 cells;
    g. Reactivity to antibodies; The cytotaxic activity is not neutralized by anti-TNF antibody, anti-lymphotoxin antibody, and anti-interferon-β antibody;
    h. N-terminal amino acid sequence; Above mentioned band B and band C are subchains of band A, respectively; N-terminus of band A is blocked. Band B and band C have commnon N-terminal amino acid sequence as follows;

Val-Val-Asn-Gly-Ile-Pro-Thr- or
Val-Val-Asn-Gly-Ile-Pro-Thr-X-Thr-Asn-Ile-Gly-X-Met-Val-Ser-Leu-
X means an unidentified amino acid.

2. A pharmaceutical composition comprised of (a) the glycoprotein of claim 1 and (b) at least one adsorption preventor selected from the group consisting of proteins and, tween 20 and tween 80, or (c) at least one stabilizing agent selected from the group consisting of proteins, carbohydrates and amino acids.

3. A pharmaceutical composition of biological factor according to claim 2, in which the protein selected as the adsorption preventor is either albumin or gelatin.

4. A pharmaceutical composition of biological factor according to claim 2, in which the nonionic detergent selected as the adsorption preventor is either Tween 80 10 or Tween 20.

5. A pharmaceutical composition of biological factor according to claim 2, in which the carbohydrate selected as the stabilizing agent of the pharmaceutical product is sorbitol, mannitol or xylitol.

6. A pharmaceutical composition of biological factor according to claim 2, in which the amino acid selected as the stabilizing agent of the pharmaceutical product is either glycine or alanine.

7. A method for stabilizing a pharmaceutical product containing the glycoprotein of claim 1, which comprises adding to the product at least one member selected from the group consisting of an adsorption preventor and a stabilizing agent.

8. A method of imparting a hepatocyte growth stimulating activity to a host in need of such treatment which comprises administering to said patient a hepatocyte growth stimulating-effective amount of the pharmaceutical composition of claim 2.

9. A method of stimulating the growth of hepatocytes which comprises contacting said hepatocytes with an effective stimulating amount of the pharmaceutical composition of claim 2.

* * * * *